(12) United States Patent
Sisto et al.

(10) Patent No.: US 7,273,856 B2
(45) Date of Patent: Sep. 25, 2007

(54) LINEAR BASIC COMPOUNDS HAVING NK-2 ANTAGONIST ACTIVITY AND FORMULATIONS THEREOF

(75) Inventors: Alessandro Sisto, Rome (IT); Valerio Caciagli, Rome (IT); Maria Altamura, Florence (IT); Alessandro Giolitti, Florence (IT); Valentina Fedi, Campi Bisenzio (IT); Antonio Guidi, Florence (IT); Danilo Giannotti, Altopascio (IT); Nicholas Harmat, Figline Valdarno (IT); Rossano Nannicini, Terranova Bracciolini (IT); Franco Pasqui, Viareggio (IT); Carlo Alberto Maggi, Florence (IT)

(73) Assignee: Menarini Ricerche S.P.A., Pomezia (IT)

( * ) Notice: Subject to any disclaimer, the term of this patent is extended or adjusted under 35 U.S.C. 154(b) by 0 days.

(21) Appl. No.: 10/494,077

(22) PCT Filed: Oct. 28, 2002

(86) PCT No.: PCT/EP02/12022

§ 371 (c)(1),
(2), (4) Date: Apr. 29, 2004

(87) PCT Pub. No.: WO03/037916

PCT Pub. Date: May 8, 2003

(65) Prior Publication Data

US 2004/0259930 A1   Dec. 23, 2004

(30) Foreign Application Priority Data

Oct. 29, 2001   (IT) .............................. FI2001A0203
Jun. 14, 2002   (IT) .............................. FI2002A0104

(51) Int. Cl.
*A61K 31/455*   (2006.01)
*A61K 31/535*   (2006.01)
*C07D 265/30*   (2006.01)
*C07D 211/82*   (2006.01)
*C07D 207/00*   (2006.01)

(52) U.S. Cl. ................ 514/86; 514/231.2; 514/252.14; 514/315; 514/356; 514/408; 544/106; 544/123; 546/329; 548/400; 549/83; 549/451

(58) Field of Classification Search ................ 546/202, 546/329; 514/324, 86, 231.2, 252.14, 356, 514/408, 315; 544/106, 123, 129, 358; 548/400; 549/83, 451
See application file for complete search history.

(56) References Cited

U.S. PATENT DOCUMENTS 5,610,176 A * 3/1997 Horwell et al. ............. 514/414
5,780,467 A * 7/1998 Dorn et al. ............... 514/236.2
6,262,069 B1 * 7/2001 Liebeschuetz et al. ...... 514/310
6,294,547 B1 * 9/2001 Oka et al. .................... 514/292
6,740,682 B2 * 5/2004 Liebeschuetz .............. 514/637
6,855,715 B1 * 2/2005 Liebeschuetz et al. ........ 514/19
6,878,725 B2 * 4/2005 Liebeschuetz et al. ...... 514/318
6,900,196 B2 * 5/2005 Liebeschuetz et al. ...... 514/183

FOREIGN PATENT DOCUMENTS

| EP | 0 394 989 A2 | 10/1990 |
| WO | WO94/04494 | 3/1994 |
| WO | WO 05/19966 | 7/1995 |
| WO | WO98/34949 | 8/1998 |
| WO | WO98/45262 | 10/1998 |
| WO | WO 00/14109 | 3/2000 |
| WO | WO 01/29066 A2 | 4/2001 |

OTHER PUBLICATIONS

International Search Report for International Application No. PCT/EP02/12022 completed Jul. 17, 2003.
D. Regoli, E. Escher, J. Mizrahi, Substance P—Structure-Activity Studies and the Development of Antagonists, Pharmacology 28: 301-320, 1984.
XP 000575827, Boden et al., Use of Dipeptide Chemical Library in the Development of Non-Peptide Tachykinin Nk3 Receptor Selective Antagonists, J. Med. Chem. 39, pp. 1664-1675, 1996.
XP 0008004494, Boyle et al., Rational Design of High Affinity Tachykinin NK2 Receptor Antagonists, Bioorganic & Medicinal Chemistry, vol. 2, No. 2, pp. 101-113, 1994.
XP 000917251, Boyle et al., Rational Sesign of High Affinity Tachykinin NK1 Receptor Antagonists, Bioorganic & Medicinal Chemistry, vol. 2, No. 5, pp. 357-370, 1994.

* cited by examiner

*Primary Examiner*—Kamal A. Saeed
*Assistant Examiner*—Susannah L. Chung
(74) *Attorney, Agent, or Firm*—Lorusso & Associates

(57) ABSTRACT

Described herein are compounds of formula (I) useful as antagonists of tachykinins in general, and in particular of neurokinin A; and the pharmaceutical formulations comprising the compounds of formula (I)

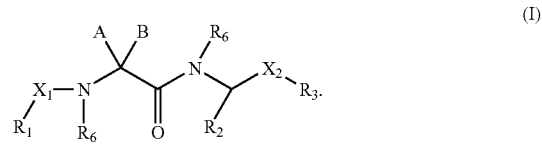

11 Claims, No Drawings

LINEAR BASIC COMPOUNDS HAVING NK-2 ANTAGONIST ACTIVITY AND FORMULATIONS THEREOF

FIELD OF THE INVENTION

The present invention relates to compounds antagonists of tachykinins in general, in particular of neurokinin A, and to their use in pharmaceutical formulations.

State of the Art

Tachykinins is a family including at least three peptides, known as Substance P, Neurokinin A (NKA) e Neurokinin B (NKB).

The research in the field of the tachykinins antagonist, mainly based on single or multiple substitution of amino acids of the sequence of the peptidic agonists of Substance P and of the other tachykinins, lead to the discovery of nonapeptides containing one or more units of D-triptophan (Regoli et al., *Pharmacol.* 28,301 (1984)). However, the problems derived from the pharmacological use of high molecular weight peptides (multiple sites of enzymatic hydrolytic attack, poor bioavailability, rapid hepatic and renal excretion) induced to search the minimum peptidic fragment which is still capable of exerting an antagonist activity. These studies lead to the detection of adequately derivatised bicyclic and monocyclic peptides, antagonist of neurokinin A (Patent Applications No. WO 9834949 and No. WO 200129066).

Various compounds have been claimed as selective antagonists of Substance P, for instance in Patent Applications No. Wo 9519966 and No. WO 9845262; but, besides being selective for NK1 receptor, these compounds have structural characteristics which are different from the compounds of the present invention, mainly the lack of a basic amino group.

Among NK1 antagonists, we can also mention those described in Patent Application No. WO 200014109; among these compounds, there is not even one alpha,alpha-disubstituted amino acid, and the basic group, when present, is in positions that are very different from those in the compounds of the invention.

Also in Patent No. EP 394 989 the compounds with NK1 activity do not usually have a basic group and do not exhibit an alpha,alpha-disubstituted-amino acid.

In *Biorganic & Med. Chem.* (1994), 2 (2), 101–113 (S. Boile et; al.) compounds with NK2 activity are described, which contain an alpha,alpha-disubstituted phenylalanine (Phe), but they do not exhibit the basic characteristics nor they can be associated to the structure described by the general formula (I).

In Patent Application No. WO 9404494 NK1 antagonists are described, which exhibit a disubstituted alpha,alpha-amino acid whose structure do not correspond to the general formula (I), in particular for the presence—among other things—of a —O—CO— group in the place of X1.

SUMMARY OF THE INVENTION

It has been surprisingly found that the present non peptidic compounds of general formula (I) as defined hereinafter, show a better behaviour in inhibiting the bonding of tachykinins onto the receptor NK2, and a better in vivo antagonist activity than that showed by the products disclosed in the above cited prior art patents.

The present invention refers therefore to linear compounds of general formula (I) comprising an alfa,alfa-disubstituted amino acid and at least an amino group capable of giving basic characteristics to the compounds

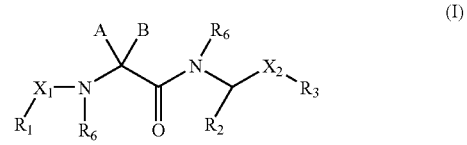

wherein:

X1 is a group selected from —NR6-CO—, —CO— and —NR6-CS—

R1 is an aryl or aryl-alkyl or aryl-ethylene group containing from 7 to 12 carbon atoms, wherein aryl indicates a group selected from the group consisting of pyridine, pyrrol, thiophene, benzene, naphthalene, imidazol, diphenyl, phenyl-thiophene, and it can be possibly substituted by one or more groups independently chosen from the group consisting of halogen, C1–C6 alkyl possibly substituted by not more than three fluorine atoms (such as a trifluoromethylic group), C1–C6 alkyloxy possibly substituted by not more than three fluorine atoms (such as a trifluoromethoxylic group), OH, —NHR10, —N(R10)2, —SR10, —CONHR10, —COR10, —COOR10, —R9COOR10, —OR9COOR10, —R9COR10, —R9CONHR10, —NHCOR10, and -nitro, wherein R10 is H or a linear or branched C1–C6 allyl chain, and R9 is a linear or branched C1–C6 alkylene chain; or the radical:

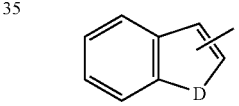

possibly substituted by one or more substituents independently chosen from halogen, C1–C6 alkyl possibly substituted by not more than three fluorine atoms (such as a trifluoromethylic group), C1–C6 alkyloxy possibly substituted by not more than three fluorine atoms (such as a trifluoromethoxylic group), —OH, —NHR10, —N(R10)2, —SR10, —CONHR10, —COR10, —COOR10, —R9COOR10, —OR9COOR10, —R9COR10, —R9CONHR10, —NHCOR10, and -nitro, wherein R10 is H or a linear or branched C1–C6 alkyl chain, and R9 is a linear or branched C1–C6 alkylene chain, and wherein D=O, S, CH2, O—CH2 or N—R7, wherein R7 is selected from the group consisting of H, a linear or branched C1–C6 alkyl chain, and acyl radical R8-CO, wherein R8 is selected from the group consisting of H and linear or branched C1–C6 alkyl chain;

R6 is selected from the group consisting of H and linear or branched C1–C6 alkyl chain;

A and B are independently selected from the group consisting of linear or branched C1–C6 alkyl chain, aryl or arylalkyl chain wherein the aryl portion is selected from the group consisting of benzothiophene, indol, pyridine, pyrrol, benzofurane, thiophene, benzene, naphthalene, imidazol, diphenyl, and it can be possibly substituted by one or more substituents independently chosen from halogen, C1–C6 alkyl chain possibly substituted by not more than three fluorine atoms (such as a trifluoromethylic group), C1–C6 alkyloxy possibly substituted by not more than three fluorine atoms (such as a trifluoromethoxylic group), —OH, —NHR10, —N(R10)2, —SR10, —CONHR10, —COR10, —COOR10, —R9COOR10, —OR9COOR10, —R9COR10, —R9CONHR10, —NHCOR10, and -nitro, wherein R10 is H or a linear or branched C1–C6 alkyl chain, and R9 is a linear or branched C1–C6 alkylene group, or A and B, together with the carbon atom to which they are bound, may form a group having general formula (II):

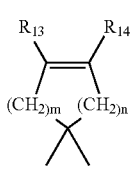

(II)

wherein the broken line indicates a possible double bond; n and m can independently be 0, 1 or 2; R13 and R14 are independently selected from the group consisting of H, C1–C6 alkyl chain, or they can be linked to form an aromatic group selected from the group consisting of benzothiophene, indol, pyridine, pyrrol, benzofurane, thiophene, benzene, naphthalene, imidazol, and biphenyl, which can be possibly substituted by one or more substituents independently selected from halogen, C1–C6 alkyl possibly substituted by not more than three fluorine atoms (such as trifluoromethylic group), C1–C6 alkyloxy chain possibly substituted by not more than three fluorine atoms (such as trifluoromethoxylic group), —OH, —NHR10, —N(R10)2, —SR10, —CONHR10, —COR10, —COOR10, —R9COOR10, —OR9COOR10, —R9COR10, —R9CONHR10, —NHCOR10, and -nitro, wherein R10 is H or linear or branched C1–C6 alkyl chain, and R9 is a linear or branched C1–C6 alkylene chain;

X2 is selected from the group consisting of —CONR6- and —CH2NR6-, wherein R6 is as described above;

R2 is selected from the group consisting of an aryl-alkyl or aryl radical wherein the aryl portion is selected from the group consisting of benzothiophene, indol, pyridine, pyrrol, benzofurane, thiophene, benzene, naphthalene, imidazol, and biphenyl, and it can be possibly substituted by one or more substituents independently selected from halogen, C1–C6 alkyl possibly substituted by not more than three fluorine atoms (such as a trifluoromethylic group), C1–C6 alkyloxy possibly substituted by not more than three fluorine atoms (such as a trifluoromethoxylic group), —OH, —NHR10, —N(R10)2, —SR10, —CONHR10, —COR10, —COOR10, —R9COOR10, —OR9COOR10, —R9COR10, —R9CONHR10, —NHCOR10, and -nitro, wherein R10 is H or a linear or branched C1–C6 alkyl chain, and R9 is a linear or branched C1–C6 alkylene chain, R3 includes at least a basic amino group, and it is represented by the general formula:

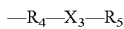

—R4—X3—R5 wherein R4 is selected from the group consisting of:
C1–C6 alkylene, C5–C8 cycloalkylene,
an aliphatic heterocycle containing at least one atom selected from N, S and O, and possibly substituted by one or two C1–C6 alkyl groups or a —COR15 group, in which R15 is selected from the group consisting of —NR11R12 and —OR11, wherein R11 and R12, independently from each other, are H or a linear or branched C1–C6 alkyl group;

aryl-alkyl or aryl wherein the aryl portion is selected from the group consisting of benzothiophene, indol, pyridine, pyrrol, benzofurane, thiophene, benzene, naphthalene, imidazol, and biphenyl, and it can be possibly substituted by one or more substituents independently selected from halogen, C1–C6 alkyl possibly substituted by not more than three fluorine atoms (such as a trifluoromethylic group), C1–C6 alkyloxy possibly substituted by not more than three fluorine atoms (such as a trifluoromethoxylic group), —OH, —NHR10, —N(R10)2, —SR10, —CONHR10, —COR10, —COOR10, —R9COOR10, —OR9COOR10, —R9COR10, —R9CONHR10, —NHCOR10, and -nitro, wherein R10 is H or a linear or branched C1–C6 alkyl group, and R9 is a linear or branched C1–C6 alkylene group, X3 is a single bond or it is selected from the group consisting of —CH2—, —CH2—CH2—, —CO—, —OCH2—CH2O—, —O—, —NH—CO—CH2—, and —NH—CO—; or —R4-X3- taken together are a group —CO—CH2—

R5 is:

an aliphatic heterocycle selected from the group consisting of pyrrolidine, piperidine, morpholine, chinuclidine, diazepan, tetrahydropyran, 1,4-dioxa-8-azaspiro[4,5]decane, possibly substituted by one or more substituents selected from the group consisting of C1–C6 alkyl, hydroxymethyl, —OH, cyanomethyl, and C1–C6 alkyloxy;

an azetidine possibly substituted by a group —(CH2)$_n$—R17, wherein R17 is selected from the group consisting of morpholine, piperidine, pyrrolidine, tetrahydropyran, and tetrahydrothiopyran;

a piperidine possibly C-substituted by a C1–C6 alkyl chain, substituted by a group X5-R18 wherein X5 is a bond or a group —C(R11)(R12)-, —CO—, —COCH2-, —CH2CH2-, and R18 is selected from the group consisting of morpholine, piperidine, pyrrolidine, tetrahydropyran, tetrahydrothiopyran, cyclohexane, dioxane, 1,4-dioxa-spiro(4,5)decyl and an aromatic selected from the group consisting of thiophene, pyridine, furane, pyrrol, thiadiazole, thiazole, and phenyl possibly substituted by one or more substituents selected from the group consisting of halogen, C1–C6 alkyl possibly substituted by not more than three fluorine atoms, C1–C6 allyloxy possibly substituted by not more than three fluorine atoms, —OH, —NHR10, —N(R10)$_2$, and —SR10 wherein R10, R11 and R12 are selected from H and linear or branched C1–C6 alkyl chain;

a piperazine possibly C-substituted by one or two C1–C6 alkyl groups, and possibly N-substituted by a group chosen from —SO$_2$NR11R12, —(CH$_2$)$_2$O(CH$_2$)$_2$OH, —CH$_2$CN, or by the group —X4-R 16 wherein X4 is a bond or it is selected from the group consisting of —CO—, —CH$_2$—, —CONR6-, —COCH$_2$— and —CO—NR6-CH$_2$—, and R16 is selected from the group consisting of pyrrolidine, morpholine, tetrahydropyran, tetrahydrofurane, dioxane, thiophene, pyridine, phenyl, naphthyl, diphenyl, pyrazol, oxazol, isoxazol and thiadiazol, possibly substituted by one or more groups selected from halogen, C1–C6 alkyl, C1–C6 alkyloxy, OH; and R6, R11 and R12 are as defined above;

an amino group selected from the group consisting of —NR11R12, —NH(CH₂)m -NR11R12, amino-tetrahydropyran, furylmethylamino, —NH(CH₂)₂O(CH₂)₂OH, wherein m ranges from 3 to 6, and R11 and R12 are as defined above an amino-cycloalkyl group possibly substituted on the ring by a group selected from OH, and NR11R12, wherein R11 and R12 are as defined above, a cycloalkyl group possibly substituted on the ring by a group selected from NR11R12, wherein R11 and R12 are as defined above;

an aryl group selected from the group consisting of thiophene, pyridine, furane or phenyl possibly substituted by one or more substituents selected from the group consisting of halogen, C1–C6 alkyl, C1–C6 alkyloxy, and OH.

Further object of the present invention are the 'retro-inverted' compounds of the present formula (1) compounds, i.e. the compounds of general formula (I) in which one or more amidic bonds are inverted.

The presence of an alpha,alpha-disubstituted amino acid and the presence of at least one amino group in R3, which gives to the compounds a strong basicity, can be considered as a peculiar structural characteristic of the products belonging to the general formula (I). Further object of the present invention are the pharmaceutically acceptable salts of the compounds of general formula (I) with organic or inorganic acids selected from the group consisting of hydrochloric acid, sulphuric acid, phosphoric acid, acetic acid, trifluoroacetic acid, oxalic acid, malonic acid, maleic acid, fumaric acid, succinic acid, tartaric acid and citric acid.

Furthermore, object of the present invention are the single enantiomers and diastereoisomers of the compounds of formula (I) or mixtures thereof, originating from the insertion into the structure of formula (I) of chiral residues or groups.

Further object of the present invention are the pharmaceutical formulations comprising the compounds of general formula (I) and the use of said compounds for preparing pharmaceutical formulations for the treatment of diseases in which neurokinin A plays a pathogenetic role.

DETAILED DESCRIPTION OF THE INVENTION

Preferred compounds of the invention are the compounds of general formula (I), wherein the aminoacidic residue of general formula (III)

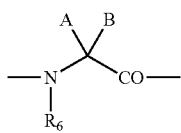

(III)

is selected from the group consisting of aminoacidic residues of α,α-• disubstituted glycine-type selected from the group consisting of 1-aminocyclohexane-1-carboxylic acid (Ac6c), 1-aminocyclopentane-1-carboxylic acid (Ac5c), 1-aminocyclopent-3-ene-1-carboxylic acid (Ac5c), 1-aminoisobutyrric acid, 1-aminoindane-1-carboxylic acid (1-Aic), 2-aminoindane-2-carboxylic acid (2-Aic), 2-aminotetraline-2-carboxylic acid (2-Atc), 2-methyl-2-ethylglycine, 2-methyl-2-isopropylglycine, 2-methyl-2-n-propylglycine, 2-methyl-2-(2-butyl) glycine, 2-methyl-2-isobutylglycine, 2-methyl-phenylalanine; and the other groups are as defined above.

Preferred compounds according to the present invention are the compounds of formula (I) wherein:

X1 is a CO group;

R1 is an aryl or aryl-ethylene group containing from 7 to 12 carbon atoms, wherein aryl is a group selected from benzene, naphthalene, and biphenyl possibly substituted by one or more groups independently selected from halogen, C1–C6 alkyl possibly substituted by not more than three fluorine atoms (such as a trifluoromethylic group), C1–C6 alkyloxy possibly substituted by not more than three fluorine atoms (such as a trifluoromethoxylic group), —OH, —NHR10, —N(R10)₂, —SR10, —CONHR10, —COR10, —COOR10, —R9COOR10, —OR9COOR10, —R9COR10, —R9CONHR10, —NHCOR10, and -nitro, wherein R10 is H or a linear or branched C1–C6 alkyl chain, and R9 is a linear or branched C1–C6 alkylene;

or it is the following radical

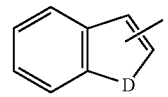

possibly substituted by one or more substituents independently selected from halogen, C1–C6 alkyl possibly substituted by not more than three fluorine atoms (such as trifluoromethylic group), C1–C6 alkyloxy possibly substituted by not more than three fluorine atoms (such as trifluoromethoxylic group), —OH, —NHR10, —N(R10)₂, —SR10, —CONHR10, —COR10, —COOR10, —R9COOR10, —OR9COOR10, —R9COR10, —R9CONHR10, —NHCOR10, and -nitro, wherein R10 is H or linear or branched C1–C6 alkyl chain, and R9 is a linear or branched C1–C6 alkylene chain, and wherein D=O, S or N—R7 wherein R7 is selected from the group consisting of H, linear or branched C1–C6 alkyl chain, acyl radical R8-CO, wherein R8 is selected from the group consisting of H and linear or branched C1–C6 alkyl chain;

R6 is selected from the group consisting of H and linear or branched C1–C6 alkyl;

the amino acidic residue of general formula (III)

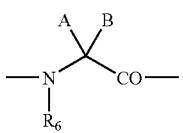

(III)

is an α,α-disubstituted glycine-type residue selected from the group consisting of 1-aminocyclohexane-1-carboxylic (Ac6c), 1-aminocyclopentane-1-carboxylic acid (Ac5c), 1-aminoindane-1-carboxylic acid (1-Aic), 1-aminocyclopentan-3-ene 1- carboxylic acid (Ac5c), 2-methyl-phenylalanine, 2-methyl-2-ethyl-glicine, R2 is a phenylmethyl group possibly substituted on the phenyl portion by one or two groups independently selected from the group consisting of halogen, C1–C6 alkyl, C1–C6 alkyloxy, and OH;

X2 is selected from —CONR6- and —CH$_2$NR6;

R3 includes at least one basic amino group and it is the following group:

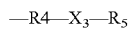

wherein

R4 is selected from the group consisting of a group —(CH$_2$)$_n$—, wherein n ranges from 1 to 3, a C5–C8 cycloalkylene group and an aliphatic heterocycle selected from piperidine, pyrrolidine or piperazine possibly substituted by one or two C1–C6 alkyl chains;

X3 is a bond or it is selected from the group consisting of —CO—, —CH$_2$—, —CH$_2$—CH$_2$—, —CO—CH$_2$—, and —NH—CO—;

R5 is selected from the group consisting of:

a) an aliphatic heterocycle selected from piperidine, pyrrolidine, morpholine, diazepan, tetrahydropyran, tetrahydrothiopyran, and 1,4-dioxa-8-azaspiro[4,5]decane, possibly substituted by one or two groups selected from C1–C6 alkyl, hydroxymethyl, cyanomethyl, C1–C6 alkyloxy, and OH;

b) an azetidine possibly substituted by a —CH$_2$)$_n$—R17 group wherein R17 is selected from the group consisting of morpholine, piperidine, pyrrolidine, tetrahydropyran, and tetrahydrothiopyran;

c) a piperidine, possibly C-substituted by a C1–C6 alkyl chain, substituted by a group X5-R18, wherein X5 is a bond or it is selected from the group consisting of —C(R11)(R12)-, —CO—, —CH$_2$CH$_2$—, and —COCH$_2$—; and R18 is selected from the group consisting of furane, morpholine, pyrrole, thiophene, tetrahydropyran, tetrahydrothiopyran, pyrrolidine, cyclohexane, cyclopentane, 1-3-dioxane, thiazole and 1,4-dioxa-spiro (4,5)decyl, possibly substituted by one or more groups selected from halogen, C1–C6 alkyl, C1–C6 alkyloxy, —OH, —NHR10, —N(R10)$_2$, and —SR10, wherein R10, R11 and R12 are selected from H and linear or branched C1–C6 alkyl;

d) a piperazine possibly C-substituted by one or two C1–C6 alkyl groups and possibly N-substituted by a group selected from —CH$_2$)$_2$O(CH$_2$)$_2$OH, —CH$_2$CN and a group X4-R16, wherein X4 is a bond or it is selected from the group consisting of —CH$_2$—,—CH$_2$—CH$_2$—, and —COCH$_2$—, and R16 is selected from the group consisting of pyridine, thiophene, tetrahydropyran, morpholine, tetrahydrofurane, and 1,3-dioxane;

e) an amino group selected from —NR11R12 and —NH—(CH$_2$)m-NR11R12 wherein R11, R12 and m are as defined above;

f) an amino-cycloalkyl possibly substituted on the ring by a group selected from OH and —NR11R12, or a cycloalkyl possibly substituted by a group NR11R12, wherein R11 and R12 are as defined above;

g) an heteroaromatic selected from pyridine and thiazole.

Amongst these compounds particularly preferred are the compounds wherein:

X1 is a —CO— group;

R1 is an aromatic group selected from the group consisting of biphenyl, phenyl-ethylene, naphthyl, phenylthiophene, benzothiophene, benzofurane, and indole possibly N-substituted by a C1–C6 alkyl group, which can be possibly substituted by one, two or three groups independently selected from the group consisting of halogen, C1–C6 alkyl possibly substituted by not more than three fluorine atoms, C1–C6 alkyloxy, OH, NHR10, and N(R10)$_2$, wherein R10 is selected from H and C1–C6 alkyl; the amino acidic residue of general formula (III) is selected from the group consisting of 1-aminocyclohexane-1-carboxylic acid (Ac6c), 1-aminocyclopentane-1-carboxylic acid (Ac5c), 1-aminoindane-1-carboxylic acid (1-Aic), 1-aminocyclopentan-3-ene 1- carboxylic acid (Ac5c), 2-methyl-phenylalanine, and 2-methyl-2-ethylglycine;

R6 is H;

R2 is a phenyl-methyl group, having the phenyl group possibly substituted by a C1–C6 alkyl group;

X2 is selected from —CONH— and CH$_2$NH—;

R3 includes at least one basic amino group having the following formula:

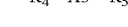

wherein:

R4 is selected from the group consisting of a group (CH$_2$)$_n$— wherein n ranges from 1 to 3, a C5–C8 cycloalkylene group selected from cyclopentylene and cyclohexylene, and an aliphatic heterocycle selected from piperidine, pyrrolidine and piperazine possibly substituted by one or two C1–C6 alkyl groups;

X3 is a bond or it is a group selected from —CO—, —CH$_2$—, —CH$_2$—CH$_2$—, and —NH—CO—;

R5 is selected from:

a) an aliphatic heterocycle selected from the group consisting of piperidine, pyrrolidine, morpholine, diazepan, tetrahydropyran, and 1,4-dioxa-8-azaspiro[4,5]decane, possibly substituted by one or two groups selected from C1–C6 alkyl, C1–C6 alkyloxy, OH, and cyanomethyl;

b) an azetidine substituted by a group —(CH$_2$)$_n$—R17, wherein R17 is tetrahydropyran;

c) a piperidine possibly C-substituted by a C1–C6 alkyl group, and substituted by a group X5-R18 wherein X5 is a bond or it is selected from the group consisting of —C(R11)(R12)-, —CO—, —CH$_2$CH$_2$—, and —COCH$_2$—, and R18 is a group selected from thiophene, tetrahydropyran, tetrahydrothiopyran, pyrrolidine, cyclohexane, cyclopentane, and 1-3-dioxane, possibly substituted by one or more groups selected from C1–C6 alkyl, —NHR10, and —N(R10)$_2$, wherein R10, R11 and R12 are selected from H and linear or branched C1–C6 alkyl;

d) a piperazine possibly C-substituted by one or two C1–C6 alkyl group, and possibly N-substituted by a group selected from —CH$_2$CN and X4–R16, wherein X4 is a bond or it is selected from —CH$_2$— and —COCH$_2$—, and R16 is selected from the group consisting of pyridine, thiophene, tetrahydropyran, morpholine, tetrahydrofurane, and 1,3-dioxane;

e) an amino group selected from —NR11R12 and —NH—(CH$_2$)m-NR11R12, wherein R11, R12 and m are as defined above;

f) an amino-cyclohexane or a cyclohexane possibly substituted on the ring by the group —NR11R12, wherein R11 and R12 are as defined above;

g) an heteroaromatic group represented by pyridine.

Amongst these compounds more preferred are the present compounds of formula (I) wherein:

X1 is a —O— group;

R1 is an aromatic group selected from the group consisting of phenyl-ethylene, naphthyl, benzothiophene, and benzofurane, possibly substituted by one, two or three groups independently selected from halogen, C1–C6 alkyl possibly substituted by not more than three fluorine atoms, C1–C6 alkyloxy, OH, NHR10, and N(R10)$_2$ wherein R10 is selected from H and C1–C6 alkyl; the amino acidic residue of general formula (m) is selected from 1-aminocyclohexane-1-carboxylic acid (Ac6c), and 1-aminocyclopentane-1-carboxylic acid (Ac5c);

R6 is H;
R2 is phenyl-methyl;
X2 is —CONH—;
R3 includes at least one basic amino group and it is the following group:

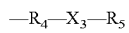

wherein
R4 is selected from —(CH$_2$)$_n$— wherein n ranges from 1 to 3, and piperidine possibly substituted by a C1–C6 alkyl group;
X3 is a bond or it is a group selected from —CO— and —CH$_2$—;
R5 is selected from:
a) an aliphatic heterocycle selected from piperidine and tetrahydropyran, possibly substituted by one or more C1–C6 alkyl groups;
b) a piperidine possibly C-substituted by a C1–C6 alkyl group, substituted by a group X5-R18 wherein X5 is a bond or it is a group selected from —C(R11)(R12)- and —CO—, and R18 is a group selected from tetrahydropyran, cyclohexane and 1-3-dioxane, possibly substituted by one or more groups selected from C1–C6 alkyl, —NHR10, and —N(R10)$_2$, wherein R10, R11 and R12 are selected from H and linear or branched C1–C6 alkyl;
c) a piperazine possibly C-substituted by one or two C1–C6 alkyl groups, and possibly N-substituted by a group X4-R16 wherein X4 is —CH$_2$—, and R16 is selected from tetrahydropyran and 1,3-dioxane.

Among the terms used for describing the present invention the following are preferred:
the term "halogen" refers to fluorine, chlorine, bromine or iodine;
the term "C1–C6 alkyl" refers to a group selected from methyl, ethyl, n-propyl, isopropyl, n-butyl, ter-butyl and, when possibly substituted by fluorine, trifluoromethyl;
the term "C1–C6 alkyloxy" refers to a group wherein the alkyl part is selected from methyl, ethyl, n-propyl, isopropyl, n-butyl, ter-butyl and, when possibly substituted by fluorine, trifluoromethyl;
the term "C1–C6 alkylene" refers to a group selected from methylene, ethylene, trimethylene, and tetramethylene;
the term "C5–C8 cycloalkylene" refers to a group selected from cyclobutylene, cyclopentylene, cyclohexylene, and cycloheptylene;
the term "cycloalkyl" refers to a group selected from cyclobutane, cyclopentane and cyclohexane.

The compounds of the present invention have shown an antagonist activity to the action of Substance P, Neurokinin A, and Neurokinin B; and they demonstrated particularly selective against the action of Neurokinin A.

Thus the present compounds of formula (I) can be used for preparing pharmaceutical formulations, possibly comprising pharmaceutically acceptable diluents and excipients commonly used in drug products, useful for the treatment and prevention of diseases in which tachykinins in general, and namely Neurokinin A, are involved as neuromodulators; as an example we can list the following diseases: respiratory pathologies, such as asthma, allergic rhinitis, and chronic obstructive bronchitis; ophthalmic diseases, such as conjunctivitis, skin diseases, such as allergic and contact dermatitis, and psoriasis, intestinal disorders, such as irritable colon, ulcerous colitis and Chron disease, gastric diseases, urinary diseases, such as cystitis and incontinence, erectile dysfunctions, diseases of the nervous central system, such as anxiety, depression and schizophreny, tumoural pathologies, autoimmunitary diseases or diseases related to AIDS, cardiovascular pathologies, neuritis, neuralgia and treatment of pain, in particular visceralgia, inflammatory processes, such as osteoarthritis or rheumatoid arthritis.

The present compounds of formula (I), as defined above, can be prepared according to methods described in literature and well known to the person skilled in the art, such as by reactions of amidic condensation, substitution, addition or reductive amination.

As an example the synthetic paths described in the general guidelines in the following reaction schemes can be followed by making the obvious and suitable changes according to the substituents.

In the following schemes, unless otherwise clearly specified, the substituents are as defined above.

For example, the compounds of general formula (I) may be obtained according to the following Scheme 1 by reacting the activated carboxylic acid derivatives of general formula (IV) with the intermediate compound of general formula (V).

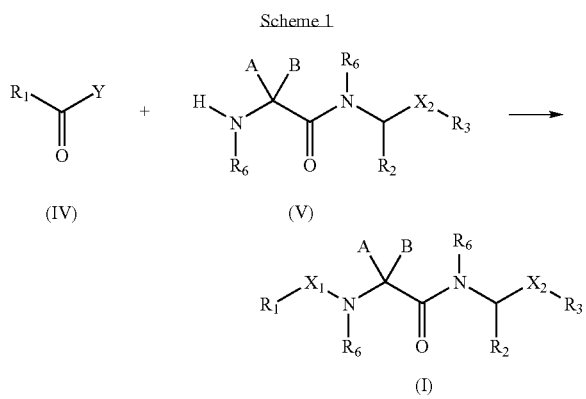

In this case, as an example, X1=CO.

Again, as an example, the compounds of general formula (I) can be obtained, as described in the following Scheme 2, according to the following sequence of reactions:
a) formation of the oxazolinone of formula (VII) starting from activated carboxylic acid derivatives of formula (IV) and amino acids of formula (VI), with suitable activating and condensing agents;
b) reaction of oxazolinone of formula (VII) with amines of formula (VIII) protected with a suitable protective group P, followed by deprotection by methods known to the person skilled in the art, to obtain the compounds of formula (IX);
c) acylation, alkylation or reductive amination with suitable reagents to yield the final compounds of formula (I).

Scheme 2

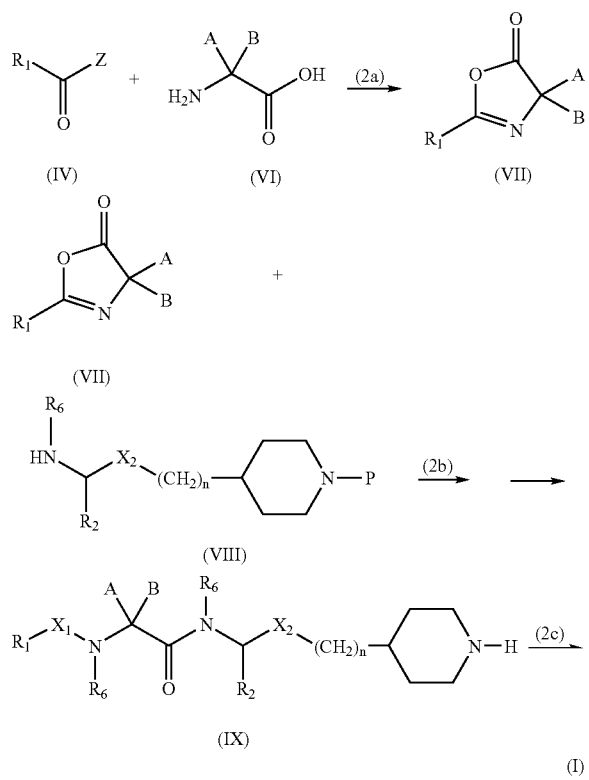

In this case, as an example, X1=CO and n=0, 1, 2.

The compounds of the present invention can occur in various isomeric forms. In fact, whereas the configuration of the carbon linked to R5 is univocally prefixed by using during the synthesis the specific isomer of the amino acid derivative, frequently the other starting products can be constituted by mixtures of stereo isomers of difficult separation.

Therefore, the compounds of the present invention can be obtained as mixtures of diastereoisomers. These mixtures can be resolved by chromatography. The compounds of formula (I) can however be used as single enantiomers as well as mixtures of isomers.

Some examples of the present compounds and of the preparation method thereof are provided in the following for illustrative and non limiting purposes of the present invention.

EXAMPLE 1

N$^\alpha$[N$^\alpha$(benzo[b]thiophenyl-2-ylcarbonyl)-1-aminocyclopentane-1-carbonyl]-D-phenylalanine-N-[3(morpholin-4-yl)propyl]amide 1a) to a solution of 1-amino-cyclopentane-1-carboxylic acid (1 g, 7.66 mmol) in 30 ml of anhydrous dichloromethane (DCM) N,O-bis(trimethylsilyl)acetamide (BSA) (3.8 ml, 15.4 mmol) is added under magnetic stirring; after 15 min trimethylchlorosylane (TMSCl) (0.38 ml, 10% of the BSA volume) is added. The amino acid is completely sylanised (the solution at the end of the addition is clear), and after about 2 hours of stirring at room temperature benzo[b]thiophene-2-carbonyl chloride (7.66 mmol) dissolved in 10 ml of DCM is added to the reaction mixture. The reaction is kept for 12 hours under stirring at room temperature.

The solution is concentrated under reduced pressure, then 50 ml of NaHCO$_3$ aq. 1M are added, and is kept under stirring for 30'. Everything is transferred into a separatory funnel, then ethyl acetate (AcOEt) (50 ml) is added; the mixture is shaked and the organic phase is removed.

The aqueous solution is acidified up to pH=1 with HCl 6N and washed with AcOEt (3×50 ml). The organic phases are collected together, transferred in a separatory funnel and washed with H$_2$O and brine up to pH=5–6. The organic phase is dried on anhydrous Na$_2$SO$_4$, then brought to dryness. The isolated residue is crystallised from acetonitrile, thus obtaining 1.4 g (4.84 mmol, yield=63%) of N$^\alpha$(benzo[b]thiophene-2-carbonyl)-1-aminocyclopentane-1-carboxylic acid.

HPLC (method E): Rt=14.04 min.

1b) To a solution in anhydrous THF (25 ml) of the product coming from Example 1a) (500 mg, 1.73 mmol), 1-ethyl-3-(3-dimethylaminopropyl)carbodiimide hydrochloride (EDC) (2.08 mmol, 0.402 g) and diisopropylethylamide (DiPEA) (5.2 mmol, 0.89 ml) are added. The solution is kept under stirring for 2 hours at room temperature. The solvent is evaporated, and the residue is dissolved with AcOEt (50 ml); the organic phase is washed with NaHCO$_3$ 1M (3×50 ml), HCl 1M (3×50 ml), saturated aqueous solution of sodium chloride (3×50 ml). The organic solution is dried on anhydrous Na$_2$SO$_4$ and then it is brought to dryness. 0.450 g of 2-(benzo[b]thiophen-2-yl)-4-cyclopentyl-1,3-oxazolin-5-one (1.66 mmol, yield=96%) are obtained.

HPLC (method E): Rt=21.86 min.

1c) To a solution in 15 ml of anhydrous THF of tert-butyloxycarbonyl-D-phenylalanine N-hydroxysuccinimidyl ester (500 mg, 1.38 mmol), N-(3-aminopropyl)-morpholine (1.328 mmol, 0.201 ml) is added. The stirring is maintained for 90 min. The solvent is then evaporated, and the residue dissolved with AcOEt (50 ml); the organic phase is washed with NaHCO$_3$ 1M (3×50 ml), HCl 1M (3×50 ml), saturated aqueous solution of sodium chloride (3×50 ml). The solution dried on anhydrous Na$_2$SO$_4$. Following the evaporation of the solvent, 474 mg of (ter-butyloxycarbonyl-D-phenylalanine-N-[3(morpholin-4-yl)propyl]amide) (1.21 mmol, yield=88%) are obtained.

HPLC (method E): Rt=10.35 mm.

1d) The product coming from Example 1c) (0.474 g, 1.21 mmol) is dissolved in 50 ml of a solution of HCl 4N in dioxane. After 30' the solvent is evaporated, and the residue is dissolved and brought to dryness with toluene and with absolute ethanol. The so obtained solid is transferred into a separatory funnel with 50 ml of NaHCO$_3$ and 50 ml of CHCl$_3$. After shaking, the organic phase is collected and the aqueous phase is washed with other 5 portions of CHCl$_3$. All the organic phases are collected, then transferred into a separatory funnel; one washing is made with a sodium chloride saturated solution. The organic phase is dried on Na$_2$SO$_4$. The solvent is evaporated. 0.291 g (1 mmol, yield=83%) of clear oil of D-phenylalanine-N-[3(morpholin4-yl)propyl]amide hydrochloride.

1e) To a solution in a mixture of 10 ml of anhydrous CH$_3$CN and 1 ml of anhydrous THF of the product coming from Example 1b) (66.5 mg; 0.245 mmol), a solution of the product coming from Example 1d) (72 mg, 0.247 mmol) in 5 ml of anhydrous CH$_3$CN is added. The reaction is allowed to reflux for 48 hours.

After removing the solvent at reduced pressure, the residue is dissolved with AcOEt (50 ml), and the solution is transferred in a separatory funnel, and washed once with a sodium chloride saturated solution. The organic phase is dried on $Na_2SO_4$ and the solvent evaporated. 135 mg of the product are obtained, which is then purified by reverse phase chromatography, using a column Hibar Merck LiChrospher 100, RP-18e (5 μm), eluents=A: $H_2O+0.1\%$ TFA; B: $CH_3CN+0.1\%$ TFA; elution with a linear gradient from 10% B at 50% B in 40 min, flow 10 ml/min; WV detection (λ=230 nm). The fractions corresponding to the peak of the product have been collected, concentrated to small volume at reduced pressure and lyophilised, yielding 0.124 mmol of $N^\alpha[N^\alpha$(benzo[b]thiophen-2-ylcarbonyl)-1-aminocyclopentane-1-carbonyl]-D-phenylalanine-N-[3(morpholin-4-yl)propyl]amide (yield=51% after purification).

MS (m/z): 563.3 (MH$^+$). (HPLC (method E): Rt=14.03 min.

EXAMPLE 2

(1R,3S)-acid-N$^\gamma${N$^\alpha$[N$^\alpha$(benzo[b]thiophen-2-ylcarbonyl)-1-aminocyclopentan-1-carboxy]-D-phenylalanil}-3-aminocyclopentan-1-carboxylic-N-[(1S,2S)-2-aminocyclohexyl]amide 2a) To a solution of (1S,2S)-diaminocyclohexane (1.14 g, 10 mmol) in 50 ml of DCM, dibenzyl dicarbonate (2 g ,7 mmol) dissolved in 20 ml of DCM is added drop by drop. When the addition is over, the obtained precipitate is filtered and dried, obtaining 0.55 g of a white solid which is the starting diamine cyclohexane. The organic filtrate (80 ml) is extracted with HCl 1N (3×10 ml) and the aqueous extract are collected, alkalinise to pH=10 and extracted with DCM (3×10 ml). The collected organic extracts are dried on anhydrous $Na_2SO_4$, then filtered and brought to dryness. The residue is dissolved in 3 ml of methanol, then ethyl acetate saturated of hydrochloric acid (EtOAc/HCl) (2 ml) is added and, subsequently, ethyl ether (20 ml) yielding a white precipitate in suspension. This precipitate is filtered and dried thus obtaining 1.44 g of (1S,2S)-N-monobenzyloxycarbonyldiaminocyclohexane hydrochloride (yield=50,5%).

HPLC (E): Rt=7.85 min.

2b) 360 mg (1.26 mmol) of the product coming from Example 2a) are dissolved in 10 ml of DMF and added with 0.296 g (1.29 mmol) of (1R,3S-N$^\gamma$-ter-butyloxycarbonyl-3-aminocyclopentan-3-carboxylic acid, 245 mg of EDC, 173 mg of HOBt and DIPEA until an alkaline reaction is achieved. The mixture is kept to react for 18 hours, then added with DCM (50 ml). The organic phase is washed with $KHSO_4$ 5% (3×50 ml), $NaHCO_3$ (3×50 ml), $NaHCO_3$(3×50 ml), $H_2O$ (3×50 ml) and dried on anhydrous $Na_2SO_4$. The organic solution is then filtered and brought to dryness yielding 0.610 g of a yellow solid, which is then dissolved in 5 ml of MeOH and added with 50 ml of $Et_2O$. A white solid precipitates and, after filtration, 440 mg (yield=68%) are obtained.

HPLC(E): Rt=15.5 min.

The residue is then dissolved in 10 ml of EtOAc and added with 20 ml of EtOAc/HCl; after 1 hour 100 ml of $Et_2O$ are added to the mixture, thus obtaining a white precipitate that, after filtration, gives 0.425 g of hydrochloride of (1R,3S)-3-aminocyclopentan-3-carboxylic-N-[(1S,2S-2-N-(benzyloxycarbonyl)aminocyclohexyl]amide acid.

HPLC(E): Rt=8.9 min.

2c) 0.425 g of the product coming from Example 2b) are dissolved in DMF (10 ml) and added with N$^\alpha$(tert-butyloxycarbonyl)-D-phenylalanine (0.312 g, 1.29 mmol), EDC (0.230 g, 1.29 mmol), HOBt (0.175 g, 1.29 mmol) and DiPEA until an alkaline reaction is achieved. The mixture is kept to react overnight, then 30 ml of DCM are added and the organic phase is washed with $KHSO_4$ 5% (3×50 ml), $NaHCO_3$ (3×50 ml), $H_2O$ (3×50 ml), and dried on anhydrous $Na_2SO_4$. After filtration and removal of the solvent, 531 mg of raw product are obtained from which, after grinding in $Et_2O$, 470 mg of a white solid (yield=83%) are obtained. HPLC(E): Rt=16.06 ml.

The release of the Boc group with EtOAc/HCl and subsequent precipitation with $Et_2O$ (70 ml) allows the isolation of 410 mg of hydrochloride of (1R,3S)-N$^\gamma$-[D-phenylalanil]-3-aminocyclopentan-3-carboxylic-N-[(1S,2S)-2-N-(benzyloxycarbonyl)aminocyclohexyl] amide acid. HPLC(E)=11.27 min.

2d) Into a 100 ml glass protected with a $CaCl_2$ tube 1.29 g (10 mmol) of 1-aminocyclohexan-1-carboxylic acid are suspended in 20 ml of DCM, and added with 5 ml of N,O-bis-(trimethylsilyl)-acetamide. The reaction mixture is kept under stirring for 2 hours until the amino acid derivative is completely dissolved. To the solution 1.8 g (0.92 mmol) of chloride of benzothiophene-2-carboxylic acid are added drop by drop in 20 ml of DCM, and the mixture is allowed to react for 1 hour at room temperature. The organic solution is then washed with water (5×50 ml), dried on anhydrous $Na_2SO_4$, filtered, brought to dryness and grinded with $Et_2O$, thus yielding 2.60 g (yield=90.2%) of a white solid of N$^\alpha$(benzo[b]thiophen-2-yl-carbonyl)-1-aminocyclohexane-1-carboxylic acid.

HPLC (method E): Rt=17.7 min.

2e) To a solution in anhydrous THF (25 ml) of the product coming from Example 2d) (0.50 g, 1.67 mmol), EDC (2.08 mmol, 0.402 g) and DiPEA (5.2 mmol, 0.890 ml) are added. The solution is maintained under stirring for 2 hours at room temperature. The solvent is then evaporated, the residue is dissolved in AcOEt (50 ml), the organic phase is washed with $NaHCO_3$ 1M (3×50 ml), HCl 1M (3×50 ml), sodium chloride saturated aqueous solution (3×50 ml). The organic solution is anhydrified on anhydrous $Na_2SO_4$ and then brought to dryness. 0.450 g of 2-(benzo[b]thiophen-2-yl)4-cyclohexyl-oxazol-5-one (1.57 mmol, yield=94%) are obtained. HPLC (method E): Rt=22.1 min.

2f) 0.176 g of the product coming from Example 2c), dissolved in 5 ml of anhydrous $CH_3CN$, are added with 82 mg of the product coming from Example 2d) and with DiPEA until an alkaline reaction is achieved. The mixture is then heated to reflux for 18 hours. The reaction mixture is then diluted with DCM (20 ml) and washed with $KHSO_4$ 5% (3×50 ml), $NaHCO_3$ (3×50 ml), $H_2O$ (3×50 ml), and dried on anhydrous $Na_2SO_4$. The mixture is filtered, brought to dryness and grinded with $Et_2O$, thus obtaining 185 mg of a white solid. HPLC(E): Rt=17.08 min.

The so obtained solid product is dissolved in 12 ml of MeOH and 1 ml of acetic acid. The resulting solution is added with 250 mg of palladium on carbon and insufflated with hydrogen for 2 hours until, under HPLC at the above described conditions, the peak at Rt=17.08 min disappears and a main peak at Rt=11.78 min appears.

After filtration of the catalyst and removal of the solvent, the reaction mixture is then purified in 10 runs of preparative chromatography using a column Vydac Peptide&Protein (250×22 mm), 10μ, eluting with $H_2O+0,1\%$ TFA (A) and $CH_3CN+0,1\%$ TFA (B) (gradient 10% to 50% of B in 110 min; flow 12 ml/min.).

The chromatographic fractions which resulted pure from HPLC analysis are collected and evaporated to yield a residue of 70 mg of (1R,3S)-acid-N$^\gamma${N$^\alpha$[N$^\alpha$(benzo[b]thiophen-2-yl-carbonyl) -1-aminocyclopentan-1-carboxy]-D-phenylalanil}-3-aminocyclopentan-1-carboxylic-N-[(1S,2S)-2-aminocyclohexyl]amide.

¹H-NMR (δ, DMSO-d₆): 1.2–1.9 (m, 22H, CH₂); 2.6 (m, 1H, CH—CO-3Ac5c); 2.9–3.20 (m, 2H, (β)CH₂—D-Phe); 3.85 (m, 1H, CH—NH, 1,2 di-NH₂-cyclohexane); 4.2 (m, 1H, CH—NH-3Ac5c); 4.45 (m, 1H, (α)CH—D-Phe)); 7.1–7.25 (m, 5H, C$_{arom}$—D-Phe); 7.45–7.85 (m, 8H, C(5) H+C(6)H+NHCH-1,2di-NH₂-cyclohexane+ NHCH-3Ac6c+NH₃⁺+NHCH—D-Phe); 7.90–8.02 (m, 2H, C(4)H+C(7)H); 8.3 (s, 1H, C(3)H); 8.9 (s, 1H, NH-1Ac5c). MS-FAB: 644,3 (M+H)⁺

With analogous methods or by obvious changes for a skilled person, the following products have been prepared:

EXAMPLE 3

N$^γ${N$^α$[N$^α$(biphen-4-ylcarboxy)-1-aminocyclopentan-1-carboxy]-D-phenylalanyl}-(1R,3S)-3-aminocyclopentane-1-carboxylic-acid-N-((1S,2S)-2-aminocyclohexyl)amide trifluoroacetate salt MS-FAB: 664.32 (M+H)⁺ HPLC (method E): Rt=10.5 min.

EXAMPLE 4

N$^γ${N$^α$[N$^α$(N-(methyl)indol-2-ylcarboxy)-1-aminocyclopentan-1-carboxy]-D-phenylalanyl}-(1R,3S)-3-aminocyclopentane-1-carboxylic-acid-N-((1S,2S)-2-aminocyclohexyl) amide trifluoroacetate salt MS-FAB: 641.32 (M+H)⁺ HPLC (method F): Rt=4.8 ml.

EXAMPLE 5

N$^γ${N$^α$[N$^α$[4-(methyl)cynnamoyl]-1-aminocyclopentan-1-carboxy]-D-phenylalanyl}-(1R,3S)-3-aminocyclopentane-1-carboxylic-acid-N-((1S,2S)-2-aminocyclohexyl)amide trifluoroacetate salt MS-FAB: 628.4 (M+H)⁺ HPLC (method F): Rt=3.37 min.

EXAMPLE 6

N$^γ${N$^α$[N$^α$(benzofuran-2-ylcarboxy)-1-aminocyclopentan-1-carboxy]-D-phenylalanyl}-(1R,3S)-3-aminocyclopentane-1-carboxylic-acid-N-(1S,2S)-2-aminocyclohexyl) amide trifluoroacetate salt MS-FAB: 628.3 (M+H)⁺ HPLC (method E): Rt=9.25 min.

EXAMPLE 7

N$^α$[N$^α$(4(methyl)cinnamoyl)-(R,S)1-aminoindane-1-carboxy]-D-phenylalanine amide-N-[(1S,3R)-3-(morpholin-4-ylmethyl)cyclopentyl]

MS-FAB: 635.2 (M+H)⁺ HPLC (method E): Rt=12.9 ml.

EXAMPLE 8

N$^γ${N$^α$[N$^α$(benzo[b]thiophen-2-ylcarbonyl)-1-aminocyclopentan-1-carboxy]-D-phenylalanyl}-(1R,3S)-3-aminocyclopentane-1-carboxylic-acid-N-((1S,2S)2-dimethylaminocyclohexyl) amide hydrochloride salt MS-FAB: 572.3 (M+H)⁺ HPLC (method E): Rt=12.0 min.

EXAMPLE 9

N$^γ${N$^α$[N$^α$(benzo[b]thiophen-2-ylcarbonyl)-1-aminocyclopentan-1-carboxy]-D-4-methyl-phenylalanyl}-(1R,3S)-3-aminocyclopentane-1-carboxylic-acid-N-(1S,2S)-2-dimethyl aminocyclohexyl)amide hydrochloride salt MS-FAB: 686.3 (M+H)⁺ HPLC (method E): Rt=12.1 min.

EXAMPLE 10

N$^γ${N$^α$[N$^α$(4-methyl-cinnamoyl)-1-aminocyclopentan-1-carboxy]-D-phenylalanyl}-(1R,3S)-3-aminocyclopentane-1-carboxylic-acid-N-((1S,2S)-2-dimethylaminocyclohexyl)amide hydrochloride salt MS-FAB: 656.3 (M+H)⁺ HPLC (method E): Rt=11.9 min.

EXAMPLE 11

N$^γ${N$^α$[N$^α$(benzofuran-2-ylcarboxy)-1-aminocyclopentan-1-carboxy]-D-phenylalanyl}-(1R,3S)-3-aminocyclopentane-1-carboxylic-acid-N-((1S,2S)-2-dimethylaminocyclohexyl)amide hydrochloride salt MS-FAB: 656.3 (M+H)⁺ HPLC (method E): Rt=11.8 min.

EXAMPLE 12

N$^γ${N$^α$[N$^α$(biphen-4-ylcarbonyl)-1-aminocyclopentan-1-carboxy]-D-phenylalanyl}-(1R,3S)-3-aminocyclopentane-1-carboxylic-acid-N-((1S,2S)-2-dimethylaminocyclohexyl)amide hydrochloride salt MS-FAB: 692.4 (M+H)⁺ HPLC (method E): Rt=12.7 min.

EXAMPLE 13

N$^γ${N$^α$[N$^α$((methyl)indol-2-ylcarboxy)-1-aminocyclopentan-1-carboxy]-D-phenylalanyl}-(1R,3S)-3-aminocyclopentane-1-carboxylic-acid-N-((1S,2S)-2-dimethylaminocyclohexyl)amide hydrochloride salt ¹H-NMR (δ, DMSO-d₆): 1.2–1.9 (m, 22H, CH₂); 2.6 (m, 1H, CH—CO-3Ac5c); 2.90–3.20 (m, 2H, (β)CH₂—D-Phe); 2.75 (m, 6H, N(CH₃)₂); 3.8 (s, 3H, 1-(CH₃) indole) 4.2 (m, 1H, CH—NH-3Ac5c); 4.45 (m, 1H, (α)CH—D-Phe); 7.10–7.25 (m, 5H, C$_{arom}$—D-Phe); 7.45–7.85 (m, 6H, C(5) H+C(6)H+NHCH-1,2di-NH₂-cyclohexane+NHCH-3Ac6c+ HN(CH₃)₂⁺+NHCH—D-Phe); 7.90–8.02 (m, 2H, C(4)H+C(7)H); 8.5 (s, 1H, C(3)H); 8.9 (bs, 1H, NH-1Ac5c). MS-FAB: 669.3 (M+H)⁺ HPLC (method E): Rt=12.2 min.

EXAMPLE 14

N$^γ${N$^α$[N$^α$(benzo[b]thiophen-2-ylcarbonyl)-(R)-α-methyl-α-ethylglycyl]-D-phenylalanyl}-(1R,3S)3-amino cyclopentane-1-carboxylic-acid-N-((1S,2S)-2-aminocyclohexyl) amide trifluoroacetate salt MS-FAB: 632.2 (M+H)⁺ HPLC (method F): Rt=5.51 mm.

EXAMPLE 15

N$^\gamma${N$^\alpha$[N$^\alpha$(4-methylcinnamoyl)-(R)-α-methyl-α-ethylglycyl]-D-phenylalanyl}-(1R,3S)-3-amino cyclopentane-1-carboxylic-acid-N-((1S,2S)-2-aminocyclohexyl) amide trifluoroacetate salt MS-FAB: 616.3 (M+H)$^+$ HPLC (method F): Rt=5.58 min.

EXAMPLE 16

N$^\gamma${N$^\alpha$[N$^\alpha$(biphenyl-4-carboxy)-1-aminocyclopentan-1-carboxy]-R-3(4(methyl) phenyl)alanyl}-(1R, 3S)-3-aminocyclopentane-1-carboxylic-acid-N-((1S, 2S)-2-aminocyclohexyl) amide hydrochloride salt MS-FAB: 678 (M+H)$^+$ HPLC (method E): Rt=12.8 min.

EXAMPLE 17

N$^\gamma${N$^\alpha$[N$^\alpha$(N-(methyl)indol-2-ylcarboxy)-1-aminocyclopentan-1-carboxy]-R-3-(4-methyl)phenyl) alanyl}-(1R,3S)-3-aminocyclopentane-1-carboxylic-acid-N-((1S,2S)-2-aminocyclohexyl)amide hydrochloride salt MS-FAB: 655 (M+H)$^+$ HPLC (method E): Rt=12.2 min.

EXAMPLE 18

N$^\gamma${N$^\alpha$[N$^\alpha$(4-(methyl)cynnamoyl)-1-aminocyclopentan-1-carboxy]-R-3[4-methyl)phenyl]alanyl}-(1R, 3S)-3-aminocyclopentane-1-carboxylic-acid-N-((1S, 2S)-2-aminocyclohexyl)amide hydrochloride salt MS-FAB: 642.2 (M+H)$^+$ HPLC (method E): Rt=12.0 mm.

EXAMPLE 19

N$^\alpha$[N$^\alpha$(benzo[b]thiophen-2-yl-carbonyl)-1-aminocyclohexan-1-carboxy]-D-phenylalanine-N-{3-[bis(n-butyl)amino]propyl}amide

EXAMPLE 20

N$^\alpha$[N$^\alpha$(benzo[b]thiophen-2-yl-carbonyl)-1-aminocyclohexan-1-carboxy]-D-phenylalanine-N-[3(morpholin-4-yl)propyl]amide

EXAMPLE 21

3-cis-N$^\gamma${N$^\alpha$[N$^\alpha$(benzo[b]thiophen-2-ylcarbonyl)-1-aminocyclohexan-1-carboxy]-D-phenylalanil}aminocyclohexan-1-carboxylic acid-N-((1R,2S)-2-aminocyclohexyl)amide $^1$H-NMR (δ, DMSO-d$_6$): 1.2–1.9 (m, 26H, CH$_2$); 2.3 (m, 1H, CH—CO-3Ac6c); 2.8–3.15 (m, 2H, (β)CH$_2$—D-Phe); 3.55 (m, 1H, CH—NH 1,2 di-NH$_2$-cyclohexane); 4.1 (m, 1H, CH—NH-3Ac6c); 4.35 (m, 1H, (α)CH—D-Phe); 7.05–7.18 (m, 5H, C$_{arom}$—D-Phe); 7.39–7.45 (m, 2H, C(5)H+C(6)H); 7.59–7.65 (m, 3H, NHCH); 7.89–7.96 (m, 2H, C(4)H+C(7)H); 8.3 (s, 1H, C(3)H); 8.42 (s, 1H, NH-1Ac6c). MS-FAB: 672,45 (M+H)$^+$ HPLC(method E): Rt=12.7 min.

EXAMPLE 22

N$^\gamma${N$^\alpha$[N$^\alpha$(benzo[b]thiophen-2-ylcarbonyl)-1-aminocyclohexan-1-carboxy]-D-phenylalanyl}-3-cis-aminocyclohexan-1-carboxylic-acid-N-(5-aminopentyl)-amide trifluoroacetate salt $^1$H-NMR (δ, DMSO-d$_6$): 1.2–1.9 (m, 24H, —CH$_2$—); 2.2 (m, 1H, CH—CO-3Ac6c); 2.7 (m,2H, NH—CH$_2$); 2.8–3.15 (m, 2H, (β)CH$_2$—D-Phe); 3.0 (m, 2H, CH$_2$—NH$_3^+$); 4.1 (m, 1H, CH—NH-3Ac6c); 4.35 (m, 1H, (α)CH—D-Phe); 7.05–7.18 (m, 5H, C$_{arom}$—D-Phe); 7.59–7.65 (m, 3H, NHCH); 7.40–7.55 (m, 5H,C(5)H+C(6)H+NH$_3^+$); 7.89–7.96 (m, 2H,C(4)H+C(7)H); 8.3 (s, 1H, C(3)H), 8.42 (s, 1H, NH-1Ac6c). MS-FAB: 660.22 (M+H)$^+$ HPLC (method E): Rt=12.4 min.

EXAMPLE 23

N$^\alpha$[N$^\alpha$(benzo[b]thiophen-2-ylcarbonyl)-1-(R)-amino-indan-1-carboxy]-D-phenylalanine-N-[3(morpholin-4-yl)propyl]amide

EXAMPLE 24

N$^\alpha$[N$^\alpha$(benzo[b]thiophen-2-ylcarbonyl)-1-aminocyclopentane-1-carboxy]-L-phenylalanine-N-[3(morpholin-4-yl)propyl]amide

EXAMPLE 25

(1R,3S) acid 3-N$^\gamma${N$^\alpha$[N$^\alpha$(benzo[b]thiophen-2-ylcarbonyl)-1-aminocyclohexan-1-carboxy]-D-phenylalanil}aminocyclopentane-1-carboxylic-N-(1S,2R)-2-aminocyclohexyl) amide $^1$H-NMR (δ, DMSO-d$_6$): 1.2–1.9 (m, 24H, CH$_2$); 2.2 (m, 1H, CH—CO-3Ac5c); 2.8–3.25 (m, 2H, (β)CH$_2$—D-Phe); 4.0 (m, 1H, CH—NH-3Ac5c); 4.25 (m, 1H, CH—NH, 1,2 di-NH$_2$—); 4.5 (m, 1H, (α)CH—D-Phe);); 7.1–7.25 (m, 5H, C$_{arom}$—D-Phe); 7.45–7.55 (m, 2H, C(5)H+C(6)H); 7.6–7.75 (m, 3H, NHCH); 7.93–8.02 (m, 2H, C(4)H+C(7)H); 8.3 (s, 1H, C(3)H); 8.42 (s, 1H, NH-1Ac6c). MS-FAB: 658.30 (M+H)$^+$ HPLC (method E): Rt=12.5 min.

EXAMPLE 26 acid-3-cis-N$^\gamma${N$^\alpha$[N$^\alpha$(benzo[b]thiophen-2-ylcarbonyl)-1-aminocyclopentane-1-carboxy]-L-phenylalanil}aminocyclohexane-1-carboxylic-N-(2-cis-aminocyclohexyl) amide

EXAMPLE 27

N$^\gamma${N$^\alpha$[N$^\alpha$(benzo[b]thiophen-2-ylcarbonyl)-1-aminocyclohexane-1-carboxy]-D-phenylalanil}-(L-(4R) amino-proline-N-(1R,2R)-aminocyclohexyl) amide MS-FAB: 659.20 (M+H)$^+$ HPLC (method E): Rt=11.4 min

EXAMPLE 28 acid-3-cis-N$^\gamma${N$^\alpha$[N$^\alpha$(benzo[b]thiophen-2-ylcarbonyl)-1-aminocyclohexan-1-carboxy]-D-phenylalanil}-aminocyclohexan-1-carboxylic-N-[(1S,2S)-2-aminocyclohexyl]amide MS-FAB: 672.24 (M+H)$^+$ HPLC (method E): Rt=12.8 min.

EXAMPLE 29 acid-3-cis-N$^\gamma${N$^\alpha$[N$^\alpha$(benzo[b]thiophen-2-ylcarbonyl)-1-aminocyclopentan-1-carboxy]-D-phenylalanil}aminocyclohexane-1-carboxylic-N-[(1S,2R)-2-dimethylaminocyclohexyl]amide

EXAMPLE 30 acid-3-cis-N$^\gamma${N$^\alpha$[N$^\alpha$(benzo[b]thiophen-2-ylcarbonyl)-1-aminocyclopentane-1-carboxy]-D-phenylalanil}aminocyclohexane-1-carboxylic-N-[(1S,2R)-aminocyclohexyl]amide $^1$H-NMR (δ, DMSO-d$_6$): 1.2–1.9 (m, 24H, CH$_2$); 2.2 (m, 1H, CH—CO-3Ac6c); 2.80–3.20 (m, 2H, (β)CH$_2$—D-Phe); 3.75 (m, 1H, CH—NH 1,2 di-NH$_2$-cyclohexane); 4.2 (m, 1H, CH—NH-3Ac6c); 4.45 (m, 1H, (α)CH—D-Phe); 7.1–7.25 (m, 5H, C$_{arom}$—D-Phe); 7.40–7.50 (m, 3H, C(5)H+C(6)H+NHCH-3Ac6c); 7.60–7.70 (m, 4H, NHCH-1,2di-NH$_2$-cyclohexane+NH$_3$$^+$); 7.85 (1H, NHCH—D-Phe);7.90–8.02 (m, 2H, C(4)H+C(7)H); 8.25 (s, 1H, C(3)H); 8.9 (s, 1H, NH-1Ac5c). MS-FAB: 658.35 (M+H)$^+$ HPLC(method E): Rt=12.0 min.

EXAMPLE 31 acid-3-cis-N$^\gamma${N$^\alpha$[N$^\alpha$(benzo[b]thiophen-2-ylcarbonyl)-1-aminocyclopentan-1-carboxy]-D-phenylalanil}aminocyclohexan-1-carboxylic-N-[(1S, 2S)-aminocyclohexyl]amide MS-FAB: 658.30 (M+H)$^+$ HPLC(method E): Rt=11.9 min.

EXAMPLE 32

N$^\alpha$[N$^\alpha$(benzo[b]thiophen-2-ylcarbonyl)-1-aminocyclopentane-1-carboxy]-D-phenylalanina amide-N-[(1S,3R)-3-(4-(methyl)piperazin-1-yl)methyl)cyclopenthyl]

EXAMPLE 33

N$^\alpha$[N$^\alpha$(benzo[b]thiophen-2-ylcarbonyl)-1-aminocyclopentan-1-carboxy]-D-phenylalanine amide-N-[(1S,3R)-3-(4-(methyl)piperazin-1-yl)carbonyl)cyclopentane

EXAMPLE 34

N$^\alpha$[N$^\alpha$(benzo[b]thiophen-2-ylcarbonyl)-D-α-methylphenylalanil]-D-phenylalanine-N-[3-(morpholin-4-yl)propyl]amide

EXAMPLE 35 acid-3-cis-N$^\alpha$[N$^\alpha$(benzo[b]thiophen-2-ylcarbonyl)-1-aminocyclohexan-1-carboxy]-D-phenylalanil}aminocyclohexan-1-carboxylic-N-((1R, 2S)-2-methylaminocyclohexyl)amide

EXAMPLE 36

N$^\alpha$[N$^\alpha$(benzo[b]thiophen-2-ylcarbonyl)-1-aminocyclopentan-1-carboxy]-D-phenylalanil}-L-(4R)amino-proline-N-(-2-cis-aminocyclohexyl) amide

EXAMPLE 37

(1R,3S) acid-3-N$^\gamma${N$^\alpha$[N$^\alpha$(benzo[b]thiophen-2-ylcarbonyl)-1-aminocyclopentan-1-carboxy]-D-phenylalanil}aminocyclopentane-1-carboxylic-N-(2-cis-aminocyclohexyl)amide $^1$H-NMR (δ, DMSO-d$_6$): 1.2–1.9 (m, 22H, CH$_2$); 2.2 (m, 1H, CH—CO-3Ac5c); 2.70–3.25 (m, 2H, (β)CH$_2$—D-Phe); 4.0 (m, 1H, CH—NH-3Ac5c); 4.2 (m, 1H, CH—NH 1,2 di-NH$_2$-cyclohexane CH—NH-3Ac6c); 4.45 (m, 1H, (α) CH—D-Phe)); 7.10–7.25 (m, 5H, C$_{arom}$—D-Phe); 7.45–7.70 (m, 7H, C(5)H+C(6)H+NHCH-1,2 di-NH$_2$-cyclohexane+NHCH-3Ac6c+NH$_3$$^+$);7.85 (d, 1H, NHCH—D-Phe);• 7.90–8.02 (m, 2H, C(4)H+C(7)H); 8.25 (s, 1H, C(3)H); 8.9 (s, 1H, NH-1Ac5c). MS-FAB: 644.3 (M+H)$^+$ HPLC(method E): Rt=11.8 min.

EXAMPLE 38

(1S,3R)-1-N{N$^\alpha$[N$^\alpha$(benzo[b]thiophen-2-ylcarbonyl)-1-aminocyclopentan-1-carboxy]-D-phenylalanil}-3-{[1S-(2S)-aminocyclohexyl)amino]methyl}amino cyclopentane

EXAMPLE 39 acid-3-cis-N{N$^\alpha$[N$^\alpha$(benzo[b]thiophen-2-ylcarbonyl)-1-aminocyclopentan-1-carboxy]-D-phenylalanil}aminocyclohexan-1-carboxylic-N-(1R, 2S)-2-dimethylaminocyclohexyl) amide

EXAMPLE 40

(1R,3S) acid-3-N{N$^\alpha$[N$^\alpha$(benzo[b]thiophen-2-ylcarbonyl)-1-aminocyclohexan-1-carboxy]-D-phenylalanil}aminocyclopentan-1-carboxylic-N-((1R,2R)2-aminocyclohexyl) amide

EXAMPLE 41

Biphenyl-4-carboxylic acid, {1-[1-(3-morpholin-4-yl-propylcarbamoyl)-2-(R)-phenyl-ethylcarbamoyl]-cyclopentyl}-amide

EXAMPLE 42

Benzofuran-2-carboxylic acid, {1-[1-(3-morpholinyl-propylcarbamoyl)-2-R)-phenyl-ethylcarbamoyl]-cyclopentyl}-amide

EXAMPLE 43

Benzo[b]thiophene-2-carboxylic acid, methyl-{1-[1-(3-morpholin-4-yl-propylcarbamoyl) 2(R)-phenyl-ethylcarbamoyl]-cyclohexyl}-amide

EXAMPLE 44

1-[3-(3,4-dichlorophenyl)-acryloylamino]-cyclopentanecarboxylic acid, [1-(3-morpholin-4-yl-propylcarbamoyl)-2-(R)-phenyl-ethyl]-amide

EXAMPLE 45

Benzo[b]thiophene-2-carboxylic acid {1-[1R-(3-morpholinyl-propylcarbamoyl)-2-phenyl-ethylcarbamoyl]-cyclopent-3-enyl}-amide MS m/z: 561.3 (M+H$^+$). HPLC (method C)Rt=12.16 min.

EXAMPLE 46

Benzo[b]thiophen-2-carboxylic acid, [1-(1-aminomethyl-2-(R)phenyl-ethylcarbamoyl)-cyclohexyl]-amide

EXAMPLE 47

1-Methyl-1H-indole-2-carboxylic acid, {1-[1-(3-morpholin-4-yl-propylcarbamoyl)-2-(R)-phenyl-ethylcarbamoyl]-cyclopentyl}-amide

EXAMPLE 48

Benzo[b]thiophene-2-carboxylic acid (1-{1-[3-(2,6-dimethyl-morpholin-4-yl)-propylcarbamoyl]-2-(R)-phenyl-ethylcarbamoyl}-cyclohexyl)-amide MS (m/z): 605.4 (MH$^+$). HPLC (method B): Rt=4.57 min.

EXAMPLE 49

1H-indol-2-carboxylic acid, {1-[1-(3-morpholin-4-yl-propylcarbamoyl)-2-(R)-phenyl-ethylcarbamoyl]-cyclopentyl}-amide

EXAMPLE 50

1-[3-(3,4-dibromophenyl)-acryloylamino]-cyclopentanecarboxylic acid [1-(3-morpholin-4-yl-propylcarbamoyl)-2-(R)-phenyl-ethyl]-amide

EXAMPLE 51

5-phenyl-thiophene-2-carboxylic acid, {1-[1-(3-morpholin-4-yl-propylcarbamoyl)-2-(R)-phenyl-ethylcarbamoyl]-cyclopentyl}-amide

EXAMPLE 52

Benzo[b]thiophene-2-carboxylic acid, (1-{1(R)-[3-(4-methyl-[1,4]diazepan-1-yl)-propylcarbamoyl]-2-phenylethyl carbamoyl}-cyclopentyl)-amide TFA salt 52a) To a suspension of 1-amino-1-cyclopentancarboxylic acid (19.2 g, 149 mmol) in 500 ml of anhydrous CH$_2$Cl$_2$, is added, under magnetic stirring, N,O-bis(trimethylsilyl)acetamide (BSA) (54 g, 268 mmol, containing 5% of TMSCl). After about 1 hour under stirring at room temperature, to this solution benzo[b]thiophene-2-carbonylchloride (29.2 g, 149 mmol) dissolved in 200 ml of CH$_2$Cl$_2$ is added in about 2 hours; the reaction mixture is kept under stirring for further 3 hours. The solution is then evaporated under reduced pressure, and the residue is treated with 200 ml of aqueous K$_2$CO$_3$ 5% for 15 min, then extracted with AcOEt (2×100 ml). The aqueous phase is then acidified with aqueous HCl 37% until complete precipitation of a white solid, which is extracted with AcOEt (2×200 ml) and dried on anhydrous Na$_2$SO$_4$. The organic phase is filtered and evaporated, thus obtaining 1-[(benzo[b]thiophene-2-carbonyl)-amino]-cyclopentanecarboxylic acid (38.7 g, 134 mmol). HPLC (method A): Rt=3.51 min.

With analogous procedures the following intermediate products have also been obtained:

1-[(6-Bromo-benzo[b]thiophene-2-carbonyl)-amino]-cyclopentanecarboxylic acid

HPLC (method A): Rt=4.08 min.

1-[(6-Bromo-naphthalene-2-carbonyl)-amino]-cyclopentanecarboxylic acid

HPLC (method A): Rt=4.03 min.

1-(3-(E)-p-Tolyl-acryloylaminocyclopentanecarboxylic acid

HPLC (method A): Rt=3.47 min.

1-[(5-Chloro-benzofuran-2-carbonyl)-amino]-cyclopentanecarboxylic acid

HPLC (method A): Rt=3.74 min.

52b) To a solution in anhydrous THF (500 ml) of the product coming from Example 52a) (16 g, 55 mmol), EDC.HCl (12.7 g, 66 mmol) and diisopropylethylamine (30 ml) are added under magnetic stirring at room temperature. The reaction mixture is kept under stirring for 4 hours, then the solvent is evaporated to dryness, and the residue is dissolved in AcOEt (1000 ml) and washed with NaHCO$_3$ 10% (3×300 ml), citric acid 10% (3×300 ml), H$_2$O (3×500 ml), then dried on Na2SO4 and brought to dryness, thus obtaining a whitish solid of 2-benzo[b]thiophen-2-yl-3-oxa-1-azaspiro[4.4]-non-1-en-4-one (13 g, 47.9 mmol).

HPLC (A): Rt=4.97 min.

With analogous procedures the following intermediate products have also been obtained:

2-(6-Bromo-benzo[b]thiophen-2-yl)-3-oxa-1-aza-spiro[4.4]-non-1-en-4-one,

HPLC(method A): Rt=5.55 min.

2-(6-Bromo-naphthalen-2-yl)-3-oxa-1-aza-spiro[4.4]-non-1-en-4-one, HPLC (method A):

Rt=5.65 min.

2-(5-Chloro-benzofuran-2-yl)-3-oxa-1-aza-spiro[4.4]non-1-en-4-one, HPLC (method A):

Rt=4.97 min.

52c) To a solution in anhydrous DMF (100 ml) of Z-D-phenylalanine (5 g, 16.7 mmol) HOBt (2.34 g, 17.6 mmol) and EDC.HCl (8.73 g, 17.55 mmol) are added under magnetic stirring. After 30 min 3-aminopropanol (1.25 g, 16.72 mmol) dissolved in DMF (60 ml) is added to the solution, and the reaction mixture is kept at room temperature for 12 hours. The mixture is then diluted with AcOEt (200 ml) and extracted with KHSO$_4$ (5% solution, 200 ml) and with NaHCO$_3$ (saturated solution, 200 ml). The organic phase, dried on Na$_2$SO$_4$, filtered and brought to dryness, is then washed with ethyl ether and the white solid in suspension is filtered to give the desired product (5.15 g, 14.5 mmol).

HPLC (method B): Rt=3.48 ml.

The product coming from the previous reaction, is deprotected by hydrogenation (H$_2$, Pd/C 10%) according to a procedure known to any person skilled in the art, to give a white solid of 2(R)-amino-N-(3-hydroxypropyl)-3-phenyl-propionamide (2.91 g, 14.5 mmol), which is used directly in the subsequent reaction.

52d) To the product coming from step 52b) (1 g, 3.7 mmol) dissolved in anhydrous DMF (40 ml), the intermediate described in 52c) (1.11 g, 5.6 mmol) is added, and the reaction is kept at room temperature under magnetic stirring for 24 hours. Then the mixture is diluted with AcOEt (150 ml) and the organic phase is washed with distilled water (3×50 ml) and a saturated solution of $NaHCO_3$ (2×50 ml), then dried on anhydrous $Na_2SO_4$ and brought to dryness to give a white solid of benzo[b]thiophene-2-carboxylic acid {1-[1(R)-(3-hydroxypropylcarbamoyl)-2-phenyl-ethylcarbamoyl]-cyclopentyl}-amide (1.51 g, 3 mmol). HPLC (method A): Rt=3.73 min.

52e) The so obtained product (1.2 g, 2.44 mmol), without further purification, is dissolved in AcOEt (30 ml). To this solution, maintained at 0° C. with an ice bath, an aqueous solution of NaBr (0.5 M, 5.35 ml, 2.68 mmol), 2,2,6,6-tetramethyl-1-piperidinyloxy (TEMPO, 3.4 mg, 0.022 mmol) is added and, drop by drop, aqueous NaClO (1.83 M, 1.55 ml). The biphasic mixture is kept at 0° C. under stirring for further 20 min, then the organic phase is separated and the aqueous phase is extracted with AcOEt (20 ml). The organic fractions are collected and washed with a buffered solution of KI (20 ml), 10% solution of $Na_2S_2O_3$ (20 ml) and $NaHCO_3$ (5%, 20 ml); they are then dried and evaporated to give a product, which is purified by flash chromatography (EtOAc/hexane, 80/20) to yield 0.82 g of a white solid of 4-[2(R)-({1-[(Benzo[b]thiophene-2-carbonyl)-amino]-cyclopentanecarbonyl}-amino)-3-phenyl-propionylamino]-propanal.

HPLC (method B): Rt=3.99 min.

The so obtained aldehyde (100 mg, 0.203 mmol) is dissolved in methanol (5 ml) and added with 1-methyl-[1,4]diazepan (115 mg, 1.01 mmol) and glacial acetic acid (0.2 ml). After the solution has been stirred for 15 min, Na(CN)$BH_3$ (20 mg, 0.32 mmol) is added to the solution. After 12 hours the solvent is evaporated under reduced pressure and the raw product is dissolved in HCl 1M. The acid extract is washed with AcOEt (10 ml) and brought up to alkaline pH by adding solid $NaHCO_3$, then it is extracted with AcOEt (2×25 ml). The organic phase is evaporated, then purified by means of preparative HPLC (colonna: Combi HT™ (SB C18, 5 μm, 100 Å, 21×50 mm), Method: $H_2O$+0.1% TFA/ MeCN+0.1% TFA, 95/5>5/95 in 10 min, flow=40 ml/min, λ=220, 270 nm) to yield benzo[b]thiophene-2-carboxylic acid (1-{1-[3-(4-methyl-[1,4]diazepan-1-yl)-propylcarbamoyl]-2-(R)-phenylethylcarbamoyl}-cyclopentyl)-amide TFA salt (40 mg, 0.067 mmol). MS (m/z): 590.5 (MH$^+$). HPLC (method A): Rt=3.05 min.

With analogous methods the following products have also been prepared:

EXAMPLE 53

Benzo[b]thiophene-2-carboxylic acid (1-{1(R)-[3-(4-methoxy-piperidin-1-yl)-propylcarbamoyl]-2-phenyl-ethylcarbamoyl}-cyclopentyl)-amide TFA salt MS (m/z): 591.3 (MH$^+$). HPLC (method A): Rt=3.64 min.

EXAMPLE 54

Benzo[b]thiophene-2-carboxylic acid (1-{1-(R)-[3-(4-hydroxy-piperidin-1-yl)-propylcarbamoyl]-2-phenylethyl carbamoyl}-cyclopentyl)-amide MS (m/z): 577.3 (MH$^+$). HPLC (method A): Rt=3.31 min.

EXAMPLE 55

Benzo[b]thiophene-2-carboxylic acid (1-{1(R)-[3-(1,4-dioxa-8-aza-spiro[4.5]dec-8-yl)-propylcarbamoyl]-2-phenyl-ethylcarbamoyl}-cyclopentyl)-amide TFA salt MS (m/z): 619.3 (MH$^+$). HPLC (method A): Rt=3.68 min.

EXAMPLE 56

Benzo[b]thiophene-2-carboxylic acid (1-{1(R)-[3-(3,5-cis-dimethylpiperazin-1-yl)-3-oxo-propylcarbamoyl]-2-phenyl-ethylcarbamoyl}-cyclopentyl)-amide TFA salt 56a) Boc-D-phenylalanine O-succinimidoester (5 g, 16.56 mmol) is dissolved in $CH_3CN$ (60 ml) and added to a solution of β-alanine (2.08 g, 16.56 mmol) and TEA (4.61 ml) in 60 ml of water. After 30 min the organic solvent is evaporated and the aqueous residue, acidified by adding HCl, is extracted with AcOEt (3×100 ml). The organic extract is washed with water, dried and brought to dryness to give a colourless oil (4.19 g, 12.08 mmol). HPLC (B): Rt=3.19 min.

The so obtained product is deprotected under standard conditions (HCl, dioxane) and the so obtained amine (2.9 g, 12 mmol) is used, without flier purification steps, in the reaction with the intermediate product described in Example 52b), in the presence of stoichiometric DIPEA, in the conditions above described, to yield 3-[2(R)-({1-[(Benzo[b]thiophene-2-carbonyl)-amino]-cyclopentanecarbonyl}-amino)-3-phenyl-propionylamino]-propionic acid (5.17 g, 10.2 mmol). HPLC (B): Rt=3.98 min.

56b) The so obtained acid (100 mg, 0.2 mmol) is caused to react with 2,6-cis-dimethylpiperazine by a standard method for the formation of the amidic bond (EDC, HOBt, $CH_2Cl_2$). The raw product of the reaction is purified by preparative HPLC (same conditions of Example 52) to yield benzo[b]thiophene-2-carboxylic acid (1-{1(R)-[3-(3,5-cis-dimethyl-piperazin-1-yl)-3-oxo-propylcarbamoyl]-2-phenyl-ethylcarbamoyl}-cyclopentyl)-amide TFA salt (25 mg, 0.035 mmol).

MS (m/z): 604.2 (MH$^+$). HPLC (method A): Rt=3.36 min.

With analogous methods, starting from suitable intermediate products as described in Example 52b) and using the obtained suitable amines when necessary, the following products have been prepared according to methods known to the skilled person:

EXAMPLE 57

Benzo[b]thiophene-2-carboxylic acid (1-{1(R)-[3-oxo-3-(4-pyridin-2-yl-piperazin-1-yl)-propylcarbamoyl]-2-phenyl-ethylcarbamoyl}-cyclopentyl)-amide MS (m/z): 653.3 (MH$^+$). HPLC (method A): Rt=3.40 min.

EXAMPLE 58

6-Bromo-naphthalene-2-carboxylic acid (1-{1(R)-[3-oxo-3-(4-pyridin-2-yl-piperazin-1-yl)propylcarbamoyl]-2-phenyl-ethylcarbamoyl}-cyclopentyl)-amide TFA salt MS (m/z): 725 (MH$^+$, monoisotopic). HPLC (method A): Rt=3.76 min.

EXAMPLE 59

6-Bromo-benzo[b]thiophene-2-carboxylic acid (1-{1(R)-[3-oxo-3-(4-pyridin-2-yl-piperazin-1-yl)-propyl-carbamoyl]-2-phenyl-ethylcarbamoyl}-cyclopentyl)-amide MS (m/z): 731 (MH+, monoisotopic). HPLC (method A): Rt=3.73 min.

EXAMPLE 60

Benzo[b]thiophene-2-carboxylic acid [1-(1(R)-{3-oxo-3-[4-(tetrahydro-pyran-4-ylmethyl)-piperazin-1-yl]-propylcarbamoyl}-2-phenyl-ethylcarbamoyl) cyclopentyl]-amide TFA salt MS (m/z): 674.2 (MH+). HPLC (method A): Rt=3.43 min.

EXAMPLE 61

Benzo[b]thiophene-2-carboxylic acid [1-(1(R)-{3-oxo-3-[4-(tetrahydro-pyran-4-yl)-piperazin-1-yl]-propylcarbamoyl}-2-phenyl-ethylcarbamoyl)-cyclopentyl]-amide TFA salt MS (m/z): 660.3 (MH+). HPLC (method A): Rt=3.40 min.

EXAMPLE 62

Benzo[b]thiophene-2-carboxylic acid (1-{1(R)-[3-(4-[1,3]dioxan-5-ylmethyl-piperazin-1-yl)$_3$-oxo-propylcarbamoyl]-2-phenyl-ethylcarbamoyl}-cyclopentyl)-amide TFA salt MS (m/z): 676.2 (MH+). HPLC (method A): Rt=3.43 ml.

EXAMPLE 63

Benzo[b]thiophene-2-carboxylic acid [1-(1(R)-{[1-(1-amino-cyclopentanecarbonyl) piperidin-4-ylmethyl]-carbamoyl}-2-phenyl-ethylcarbamoyl)-cyclopentyl]-amide MS (m/z): 644.3 (MH+). HPLC (method A): Rt=3.55 min.

EXAMPLE 64

Benzo[b]thiophene-2-carboxylic acid [1-(1(R)-{3-oxo-3-[4-(tetrahydro-furan-2(R)-ylmethyl)-piperazin-1-yl]-propylcarbamoyl}-2-phenyl-ethylcarbamoyl)-cyclopentyl]-amide TFA salt MS (m/z): 660.2 (MH+). HPLC (method A): Rt=3.68 min.

EXAMPLE 65

Benzo[b]thiophene-2-carboxylic acid (1-{1(R)-[3-(4-cyanomethyl-piperazin-1-yl)-3-oxo-propylcarbamoyl]-2-phenyl-ethylcarbamoyl}-cyclopentyl)-amide MS (m/z): 615.1 (MH+). HPLC (method A): Rt=3.79 min.

EXAMPLE 66

Benzo[b]thiophene-2-carboxylic acid {1-[2-phenyl-1(R)-(1-pyridin-2-ylmethyl-piperidin-4-ylcarbamoyl)-ethylcarbamoyl]-cyclopentyl}-amide TFA salt 66a) Z-D-phenylalanina (3.28 g, 11 mmol) is caused to react with N-Boc-(4-amino)piperidine hydrochloride (2.6 g, 11 mmol) under the usual conditions for peptidic coupling (HOBt, EDC, DIPEA, $CH_2Cl_2$) as described in Example 56b). The so obtained adduct (5 g, 10.3 mmol), after a simple extractive processing, is hydrogenated in the presence of Pd/C as the catalyst, so to obtain 4-(2(R)-amino-3-phenyl-propionylamino)-piperidine-1-carboxylic acid tert-butyl ester (3.21 g, 9.27 mmol).

HPLC (method B): Rt=3.22 min.

With analogous procedures the following intermidiates have also been obtained:

4-[(2(R-amino-3-phenyl-propionylamino) methyl]-piperidine-1-carboxylic acid tert-butyl ester 4-[2-(2(R)-amino-3-phenyl-propionylamino)-ethyl]-piperidine-1-carboxylic acid tert-butyl ester (in this case, the N-Boc-4-aminoethyl)piperidine obtained starting from the corresponding alcohol by obvious reaction for a skilled person, has been used).

66b) The compound obtained as in Example 66a) (1.69 g, 4.87 mmol) is reacted with DMF at room temperature for 24 hours with the oxazolinone described in Example 52b) (1.29 g, 4.8 mmol). The so obtained intermediate (2.9 g, 4.7 mmol, HPLC (B): Rt=4.55 min), after a simple extractive working, is deprotected by reaction with TFA in $CH_2Cl_2$, to yield benzo[b]thiophene-2-carboxylic acid {1-[2-phenyl-1(R)-(piperidin-4-ylcarbamoyl)-ethylcarbamoyl]-cyclopentyl}-amide TFA salt. MS (m/z): 519.2 (MH+). HPLC (method A): Rt=3.29 mm.

With analogous methods the following compounds have been prepared:

benzo[b]thiophene-2-carboxylic acid (1-{2-phenyl-1(R)-[(piperidin-4-yl-methyl)-carbamoyl]-ethylcarbamoyl}-cyclopentyl)-amide TFA salt MS (m/z): 533.3 (MH+). HPLC (method A): Rt=3.29 min.

benzo[b]thiophene-2-carboxylic acid {1-[2-phenyl-1(R)-(2-piperidin-4-yl-ethyl carbamoyl) -ethylcarbamoyl]-cyclopentyl}-amide TFA salt MS (m/z): 547.3 (MH+). HPLC (method A): Rt=3.39 min.

66c) 200 mg (0.31 mmol) of benzo[b]thiophene-2-carboxylic acid {1-[2-phenyl-1(R)-(piperidin-4-ylcarbamoyl)-ethylcarbamoyl-cyclopentyl}-amide are used for the reaction of reductive amination with pyridine 2-carboxaldehyde (64 mg, 0.6 mmol), to yield, after purification by preparative HPLC according to the method already described in the previous Examples, the desired product benzo[b]thiophene-2-carboxylic acid {1-[2-phenyl-1(R)-(1-pyridin-2-ylmethyl-piperidin-4-ylcarbamoyl)-ethylcarbamoyl]-cyclopentyl}-amide TFA salt (120 mg, 0.16 mmol).

MS (m/z): 610.3 (MH+). HPLC (method A): Rt=3.58 min.

In analogy to what described in Example 66c), the reaction in DMF, at room temperature and for times ranging from 12 to 48 hours, of the intermediate products described in Example 66a) with oxazolinones described in Example 52b), and the reaction of the intermediate products described in Example 66a) with 1-(3-(E)$_p$-Tolyl-acryloylamino)-cyclopentanecarboxylic acid described in Example 52a) under conditions of peptidic coupling, gives, after deprotection of the amino groups, intermediates analogous to those described in Example 66b). Such intermediates are alkylated under conditions which are widely reported in the literature and well known to any person skilled in the art, such as:

aldehyde or ketone, cyanoborohydride supported on resine in anhydrous $CH_2Cl_2$
aldehyde or ketone, $Na(AcO)_3BH$, in $CH_2Cl_2$ or THF
alkyl halide, KI, DiPEA in DMF, or under the conditions described above in Example 52d).

With the synthetic procedure described in Example 66 the following products have been prepared:

EXAMPLE 67

Benzo[b]thiophene-2-carboxylic acid (1-{2-phenyl-1R)-[1-(tetrahydro-pyran-4-ylmethyl)-piperidin-4-ylcarbamoyl]-ethylcarbamoyl}-cyclopentyl)-amide TFA salt MS (m/z): 617.3 ($MH^+$). HPLC (method A): Rt=3.44 min.

EXAMPLE 68

Benzo[b]thiophene-2-carboxylic acid [1-(2-phenyl-1(R)-{1-[2-(tetrahydro-pyran-4-yl)-ethyl]-piperidin-4-ylcarbamoyl}-ethylcarbamoyl)-cyclopentyl]-amide TFA salt MS (m/z): 631.3 ($MH^+$). HPLC (method A): Rt=3.57 min.

EXAMPLE 69

6-Bromo-benzo[b]thiophene-2-carboxylic acid [1-(2-phenyl-1(R)-{[1-(tetrahydro-pyran-4-ylmethyl)-piperidin-4-ylmethyl]-carbamoyl}-ethylcarbamoyl)-cyclopentyl]-amide TFA salt MS (m/z): 709 ($MH^+$, isotopic pattern of Br). HPLC (method A): Rt=3.82 mm. $^1H$ NMR (400 MHz): (δ, DMSO-$d_6$) 1.12–2.13 (m, 17 H); 2.17–2.30 (m, 1H); 2.74–3.00 (m, 5H), 3.02–3.38 (m, 5H); 3.44–3.57 (m, 2H); 3.80–3.93(m, 2H); 4.39–4.50 (m, 1H); 7.11–7.24 (m, 5H); 7.55–7.66 (m, 2H); 7.85–7.92 (m, 1H); 7.93–7.98 (m, 1H); 8.30 (s, 1H); 8.34–8.38 (m, 1H); 8.97 (s, 1H); 8.78 and 9.01 (2 broad signal, 1H total).

EXAMPLE 70

Benzo[b]thiophene-2-carboxylic acid (1-{1-(R)-[(1-isopropyl-piperidin-4-ylmethyl)-carbamoyl]-2-phenyl-ethylcarbamoyl}-cyclopentyl)-amide MS (m/z): 575.3 ($MH^+$). HPLC (method A): Rt=3.56 min.

EXAMPLE 71

Benzo[b]thiophene-2-carboxylic acid [1-(2-phenyl-1(R)-{[1-(tetrahydro-pyran -4-ylmethyl)-piperidin-4-ylmethyl]-carbamoyl}-ethylcarbamoyl)-cyclopentyl]-amide MS (m/z): 631.3 ($MH^+$). HPLC (method A)=Rt=3.51 min. $^1H$ NMR (500 MHz): (δ, DMSO-$d_6$) amongst the others 0.99–1.14 (m, 4H); 2.18–2.29 (m, 1H), 2.65–2.75 (m, 2H); 2.78–3.02 (m, 3H); 3.75–3.85 (m, 2H); 4.41–4.50 (m, 1H); 7.09–7.23 (m, 5H); 7.43–7.52 (m, 3H); 7.86 (d, 1H, J=8.6); 7.94–8.07 (m, 2H); 8.30 (s, 1H); 8.89 (s, 1H).

EXAMPLE 72

6-Bromo-naphthalene-2-carboxylic acid [1-(2-phenyl-1(R)-{[-(tetrahydro-pyran-4-ylmethyl)-piperidin-4-ylmethyl]-carbamoyl]-ethylcarbamoyl)-cyclopentyl]-amide MS (m/z): 703.3 ($MH^+$, isotopic pattern of Br). HPLC (method A): Rt=3.88 ml. $^1H$ NMR (600 MHz): (δ, DMSO-$d_6$) 0.90–1.11 (m, 4H); 1.18–1.29 (m, 1H); 1.38–1.73 (m, 12H); 1.74–1.82 (m, 1); 1.87–1.91 (m, 2H); 1.92–1.99 (m, 1H); 2.27–2.34 (m, 1H); 2.50–2.56 (m, 2H); 2.81–2.89 (m, 2H); 2.94–3.02 (m, 1H); 3.16–3.28 (m, 3H); 3.75–3.83 (m, 2H); 4.44–4.50 (m, 1H); 7.11–7.21 (m, 5H); 7.46 (t, 1H, J=5.77 Hz); 7.71–7.75 (m, 1H); 7.82(d, 1H, J=8.65 Hz); 7.98–8.04 (m, 3H); 8.29–8.31 (m, 1H); 8.53 (s, 1H); 8.83 (s, 1H).

EXAMPLE 73

Benzo[b]thiophene-2-carboxylic acid [1-(2-phenyl-1(R)-{[1-(tetrahydro-pyran-4-yl)-piperidin-4-ylmethyl]-carbamoyl}-ethylcarbamoyl)-cyclopentyl]-amide MS (m/z): 614.4 ($MH^+$). HPLC (method A): Rt=3.46 min.

EXAMPLE 74

1-(3-E-p-Tolyl-acryloylamino)-cyclopentanecarboxylic acid (2-phenyl-1(R)-{[1-(tetrahydro-pyran-4-ylmethyl)-piperidin-4-ylmethyl]-carbamoyl}-ethyl)-amide TFA salt MS (m/z): 615.4 ($MH^+$). HPLC (method A): Rt=3.56 min. $^1H$ NMR (400 MHz): (δ, DMSO-$d_6$) amongst the others 1.13–1.25 (m, 2H); 2.15–2.23 (m, 1H); 2.34 (s, 3H); 3.80–3.87 (m, 2H); 4.36–4.44 (2 m, 1H total); 6.68 and 6.69 (2 d, 1H total J=15.81 for both); 7.13–7.30 (m, 7H); 7.375 and 7.38 (2 d, 1 H total, J=15.81 for both); 7.45–7.51 (m, 2H); 7.66 and 7.73 (2 t,1 H total, J=5.8 Hz for both); 7.82 and 7.83 (2 d, 1H total, J=8.67 for both); 8.54 and 8.55 (2 s, 1H total); 8.80 and 8.97 (2 broad signal, 1H total).

EXAMPLE 75

Benzo[b]thiophene-2-carboxylic acid [1-(2-phenyl-1(R)-{2-[1-(tetrahydro-pyran-4-ylmethyl)piperidin-4-yl]-ethylcarbamoyl}-ethylcarbamoyl)cyclopentyl]-amideTFA salt MS (m/z): 645.5 ($MH^+$). HPLC (method A): Rt=3.63 min.

EXAMPLE 76

6-Bromo-naphthalene-2-carboxylic acid (1-{1(R)-[(1-ethyl-piperidin-4-ylmethyl)-carbamoyl]-2-phenyl-ethylcarbamoyl}-cyclopentyl)-amide MS (m/z): 633.4 ($MH^+$, con isotopic pattern of Br). HPLC (method A): Rt=3.86 min.

EXAMPLE 77

Benzo[b]thiophene-2-carboxylic acid [1-(2-phenyl-1 (R)-{2-[1-(tetrahydro-pyran-4-yl)-piperidin-4-yl]-ethylcarbamoyl}-ethylcarbamoyl)cyclopentyl]-amide TFA salt MS (m/z): 631.4 (MH$^+$). HPLC (method A): Rt=3.53 min.

EXAMPLE 78

Benzo[b]thiophene-2-carboxylic acid {1-[2-phenyl-1(R)-({1-[2-(tetrahydro-pyran-4-yl)-ethyl]-piperidin-4-ylmethyl}-carbamoyl)-ethylcarbamoyl-cyclopentyl}-amide MS (m/z): 645.3 (MH$^+$). HPLC (method A): Rt=3.61 min.

EXAMPLE 79

Benzo[b]thiophene-2-carboxylic acid (1-{1(R)-[(1-cyclohexylmethyl-piperidin-4 ylmethyl)-carbamoyl]-2-phenyl-ethylcarbamoyl}-cyclopentyl)-amide MS (m/z): 629.3 (MH$^+$). HPLC (method A): Rt=4.11 min.

EXAMPLE 80

6-Bromo-naphthalene-2-carboxylic acid [1-(2-phenyl-1(R)-{[1-(tetrahydro-pyran-4-yl)-piperidin-4-ylmethyl]-carbamoyl}-ethylcarbamoyl)-cyclopentyl]-amide MS (m/z): 689.3 (MH$^+$, isotopic pattern of Br). HPLC (method A): Rt=3.83 min.

EXAMPLE 81

Benzo[b]thiophene-2-carboxylic acid [1-(2-phenyl-1 (R)-{[1-(tetrahydro-thiopyran-4-yl)-piperidin-4-ylmethyl]-carbamoyl}-ethylcarbamoyl)-cyclopentyl]-amide TFA salt MS (m/z): 633.5 (MH$^+$). HPLC (method A): Rt=3.79 min.

EXAMPLE 82

Benzo[b]thiophene-2-carboxylic acid [1-(2-phenyl-1 (R)-{[1-(tetrahydro-thiopyran-4-ylmethyl)-piperidin-4-ylmethyl]-carbamoyl}-ethylcarbamoyl)cyclopentyl]-amide MS (m/z): 647.3 (MH$^+$). HPLC (method A): Rt=3.91 min.

EXAMPLE 83

1-((E)-3-p-Tolyl-acryloylamino)-cyclopentanecarboxylic acid {2-phenyl-1(R)-[(1-thiophen-2-ylmethyl-piperidin-4-ylmethyl)-carbamoyl]-ethyl}-amide TFA salt MS (m/z): 613.3 (MH$^+$). HPLC (method A): Rt=3.82 ml.

EXAMPLE 84

6-Bromo-naphthalene-2-carboxylic acid (1-{2-phenyl-1(R)-[2-(1-pyrrolidin-2(S)-ylmethyl-piperidin-4-yl)ethylcarbamoyl]-ethylcarbamoyl}-cyclopentyl) amide TFA salt MS (m/z): 702 (MH$^+$, isotopic pattern of Br). HPLC (method A): Rt=3.55 min.

EXAMPLE 85

6-Bromo-naphthalene-2-carboxylic acid (1-{2-phenyl-1(R)-[(piperidin 4-ylmethyl)-carbamoyl]-ethylcarbamoyl}-cyclopentyl)-amide MS (m/z): 605 (MH$^+$, isotopic pattern of Br). HPLC (method A): Rt=3.71 min.

EXAMPLE 86

1-(3-p-Tolyl-acryloylamino)-cyclopentanecarboxylic acid (2-phenyl-1(R)-{2-[1-(tetrahydro-pyran-4-ylmethyl)-piperidin-4-yl]-ethylcarbamoyl}-ethyl)-amide TFA salt MS (m/z): 628.4 (MH$^+$). HPLC (method A): Rt=3.60 min.

EXAMPLE 87

Benzo[b]thiophene-2-carboxylic acid (1-{1(R)-[2-(1-cyanomethyl-piperidin-4-yl)-ethylcarbamoyl]-2-phenyl-ethylcarbamoyl}-cyclopentyl)-amide TFA salt MS (m/z): 586.3 (MH$^+$). HPLC (method A): Rt=3.60 min.

EXAMPLE 88

Benzo[b]thiophene-2-carboxylic acid (1-{1(R)-[(1-[1,3]dioxan-5-ylmethyl-piperidin-4-ylmethyl)carbamoyl]-2-phenyl-ethylcarbamoyl}-cyclopentyl)-amide TFA salt MS (m/z): 633.3 (MH$^+$). HPLC (method A): Rt=3.50 min.

EXAMPLE 89

6-Bromo-naphthalene-2-carboxylic acid (1-{1(R)-[(1-[1,3]dioxan-5-ylmethyl-piperidin-4-ylmethyl)-carbamoyl]-2-phenyl-ethylcarbamoyl}-cyclopentyl)-amide MS (m/z): 705.3 (MH$^+$, isotopic pattern of Br). HPLC (method A): Rt=3.62 min.

EXAMPLE 90

Benzo[b]thiophene-2-carboxylic acid (1-{1(R)-[(1-[1,3]dioxan-2-ylmethyl-piperidin-4-ylmethyl)-carbamoyl]-2-phenyl-ethylcarbamoyl}-cyclopentyl)-amide MS (m/z): 633.4 (MH$^+$). HPLC (method A): Rt=3.66 min.

EXAMPLE 91

5-Chloro-benzofuran-2-carboxylic acid (1-{1(R)-[(1-[1,3]dioxan-5-ylmethyl-piperidin-4-ylmethyl)-carbamoyl]-2-phenyl-ethylcarbamoyl}-cyclopentyl)-amide MS (m/z): 651.3 (MH+, isotopic pattern of Cl). HPLC (method A): Rt=3.73 ml.

EXAMPLE 92

5-Chloro-benzofuran-2-carboxylic acid [1-2-phenyl-1(R)-{[1-(tetrahydro-pyran-4-yl)-piperidin-4-ylmethyl]-carbamoyl}-ethylcarbamoyl)-cyclopentyl]-amide MS (m/z): 635.3 (MH+, isotopic pattern of Cl). HPLC (method A): Rt=3.70 min.

EXAMPLE 93

5-Chloro-benzofuran-2-carboxylic acid [1-(2-phenyl-1(R)-{[1-(tetrahydro-thiopyran-4-yl)-piperidin-4-ylmethyl]-carbamoyl}-ethylcarbamoyl)cyclopentyl]-amide MS (m/z): 651.3 (MH+, isotopic pattern of Cl). HPLC (method A): Rt=3.98 min.

EXAMPLE 94

Benzo[b]thiophene-2-carboxylic acid [1-(1(R)benzyl-2-{2-[1-(thiophen-2-yl-acetyl)-piperidin-4-yl]-ethylamino}-ethylcarbamoyl)-cyclopentyl]-amide TFA salt 94a) 1-trityl-2-(R)-benzyl-1,2-ethylendiamine.

To a suspension of 24 g of D-phenylalaninamide in DMF (200 ml) 41.0 g di trityl chloride are added under stirring at room temperature and, after 1 hour, 80 ml of TEA diluted in 100 ml of DMF are also added. Stirring is maintained for 10 hours, then the solvent is evaporated, the residue is dissolved in ethyl acetate and washed with NaCl aq. 10%, citric acid aq. 10% and again with NaCl aq. 10%. After drying and evaporation, the residue is then dissolved in 200 ml of DMF. To th eso obtained solution 2000 ml of distilled water are added drop by drop. A precipitate is obtained, which is first brought to dryness then dissolved in 200 ml of THF and this solution is added, drop by drop, in 20 min at 0° C., under stirring and under nitrogen atmosphere, to a solution of 400 ml of LiAlH$_4$ 0.62 M in THF. The mixture is heated and maintained under reflux for 4 hours. After the mixture has been brought to 0° C., 15 ml of distilled water, 15 ml of NaOH aq. 15% and 45 ml of water are added in this order. By filtration of the so obtained precipitate, 1-trityl-2-(R)-benzyl 1,2-ethylendiamine is obtained.

94b) To a solution of 1-trityl-2-(R)-benzyl-1,2-ethylendiamine coming from Example 94a) (21.6 g, 55 mmol) in anhydrous CH$_2$Cl$_2$ (300 ml) and TEA (8.4 ml, 60.5 mmol) maintained at 0° C., 2-nitrobenzensolphonylchloride (12.2 g, 55 mmol) is added in small portions. Once the addition is over, the mixture is kept under stirring at room temperature for 4 hours more, then it is washed with NaCl aq. 15% (150 ml), NaHCO$_3$ aq. 5% (150 ml) and again with NaCl aq. 15% (150 ml). The organic phase dried and evaporated at reduced temperature yield a solid product, which is then dissolved in 150 ml of CH$_3$CN, cooled at 0° C. and treated with an excess of HCl in dioxane. After 2 hours at room temperature the solvent is evaporated to dryness, and the solid residue is dissolved in ethyl ether and filtered to yield a white solid of N-(2(R)-Amino-3-phenyl-propyl)-2-nitro-benzenesulphonamide hydrochloride.

HPLC (method A): Rt=2.70 min.

94c) The oxazolinone described in Example 52b) (407 mg, 1.5 mmol) and the intermediate 94b) described above (670 mg, 1.5 mmol) are dissolved in DMF (8 ml), added with TEA (0.64 ml, 4.5 mmol) and maintained at 80° C. under stirring for 2 hours. The residue obtained from evaporation of the solvent is dissolved with AcOEt (30 ml) and washed with HCl 1M (10 ml), NaHCO$_3$ (5%, 10 ml), and NaCl aq. 15% (10 ml). The so obtained raw product is purified by flash chromatography (AcOEt/hexane 1/1) to give 0.5 g (0.8 mmol) of the intermediate benzo[b]thiophene-2-carboxylic acid {1-[1(R)-benzyl-2-(2-nitro-benzenesulphonylamino)-ethylcarbamoyl]-cyclopentyl}-amide.

HPLC (method B): 4.74 min.

94d) 1.2 g (3.36 mmol, 3 mmol/g of loading) of triphenylphosphinic resin are maintained to swell for 30 min in CH$_2$Cl$_2$ (25 ml) under balancing stirring; to the suspension the intermediate described in Example 94c) (0.5 g, 0.84 mmol), N-Boc-4-hydroxyethyl-piperidine (600 mg, 2.52 mmol) and tert-butyl-diazodicarboxylate (600 mg, 2.52 mmol) are added. After 16 hours under stirring the resin is removed by filtration and the solution is brought to small volume (10 ml). 5 ml of trifluoroacetic acid are added under stirring. After 1 hour the solution is brought to dryness, the residue is dissolved with AcOEt (30 ml) and the solution washed with Na$_2$CO$_3$ aq. 5% (15 ml) e NaCl aq. 15% (10 ml), dried and evaporated Benzo[b]thiophene-2-carboxylic acid (1-{1(R)-benzyl-2-[(2-nitro-benzenesulphonyl)-(2-piperidin-4-yl-ethyl)-amino]-ethylcarbamoyl}-cyclopentyl)-amide is obtained as a foamy solid (553 mg, 0.77 mmol).

HPLC (method A): Rt=4.20 min

95e) The product coming from the previous step (60 mg, 0,084 mmol) is dissolved in CH$_2$Cl$_2$ (2 ml) and to this solution 60 μl of TEA and 13.5 μl of thiophen-2-yl-acetyl chloride are added. The magnetic stirring is maintained for 12 hours, then the solvent is evaporated and the residue, dissolved with AcOEt (10 ml), is washed with Na$_2$CO$_3$ aq. 5% (2×5 ml). The raw product obtained from evaporation of the solvent (60 mg, 0.07 mmol), is dissolved in DMF (3 ml) and treated with diazabicycloundecene (DBU, 32 mg, 0.21 mmol) and 2-mercaptoethanol (17 mg, 0.21 mmol) for 12 hours. The residue obtained from evaporation of the solvent at reduced pressure is washed with ethyl ether and purified by preparative HPLC yielding 10 mg (0.013 mmol) of benzo[b]thiophene-2-carboxylic acid [1-(1(R)-benzyl-2-{2-[1-(thiophen-2-yl-acetyl)-piperidin-4-yl]-ethylamino}-ethylcarbamoyl)-cyclopentyl]-amide TFA salt as white lyophilic product.

MS (m/z): 657.3 (MH+). HPLC (method A): Rt=4.12 min.

EXAMPLE 95

Benzo[b]thiophene-2-carboxylic acid 1-(1(R)-{2-[(1-amino-cyclohexanecarbonyl)-amino]-ethylcarbamoyl}-2-phenyl-ethylcarbamoyl)cyclopentyl]-amide

[2-(2(R)-Amino-3-phenyl-propionylamino)-ethyl]-carbamic acid tert-butyl ester (200 mg, 0.65 mmol), obtained by coupling of N-Boc-ethylendiamine and Z-D-phenylalanine succinimidoester followed by hydrogenation, is added to a solution of 2-benzo[b]thiophen-2-yl-3-oxa-1-azaspiro[4.4]-non-1-en-4-one (176 mg, 0.65 mmol) in DMF and maintained under magnetic stirring at room temperature for 48 hours. The so obtained product is deprotected (HCl, dioxane), acylated with 1-Boc-amino-1-cyclohexancarboxylic acid (156 mg, 0.65 mmol), by standard activation as described above, then again deprotected (HCl, dioxane). The raw product obtained from extractive work up is purified by flash chromatography (eluent: CHCl$_3$/MeOH 9:1) to give benzo[b]thiophene-2-carboxylic acid [1-(1(R)-{2-[(1-amino-cyclohexanecarbonyl)-amino]ethylcarbamoyl}-2-phenyl-ethylcarbamoyl)-cyclopentyl]-amide (160 mg, 0.27 mmol).

MS (m/z): 604.3 (MH$^+$). HPLC (method A): Rt=3.58 min.

With analogous methods the following products have been prepared:

EXAMPLE 96

Benzo[b]thiophene-2-carboxylic acid [1-(1(R)-{[1-(1-aminocyclohexanecarbonyl)-piperidin-4-ylmethyl]-carbamoyl}-2-phenyl-ethylcarbamoyl)-cyclopentyl]-amide TFA salt MS (m/z): 658.3 (MH$^+$). HPLC (method A): Rt=3.62 min.

EXAMPLE 97

6-Bromo-naphthalene-2-carboxylic acid [1-(1(R)-{[1-(1-amino-cyclohexanecarbonyl)-piperidin-4-ylmethyl]-carbamoyl}-2-phenyl-ethylcarbamoyl)-cyclopentyl]-amide MS (m/z): 730.2 (MH$^+$, isotopic pattern of Br). HPLC (method A): Rt=4.00 min.

EXAMPLE 98

6-Bromo-naphthalene-2-carboxylic acid [1-(2-phenyl-1(R)-{2-[1-(pyrrolidine-2(S)-carbonyl)-piperidin-4-yl]-ethylcarbamoyl}-ethylcarbamoyl)-cyclopentyl]-amide MS (in/z): 716.3 (MH$^+$, isotopic pattern of Br). HPLC (method A): Rt=3.95 min.

EXAMPLE 99

6-Bromo-naphthalene-2-carboxylic acid [1-(2-phenyl-1(R)-{2-[1-(pyrrolidine-2(R)-carbonyl)-piperidin-4-yl]-ethylcarbamoyl}-ethylcarbamoyl)-cyclopentyl]-amide MS (m/z): 716.3 (MH$^+$, isotopic pattern of Br). HPLC (method A): Rt=3.97 min.

EXAMPLE 100

Benzo[b]thiophene-2-carboxylic acid [1-(2-phenyl-1(R)-{2-[4-(thiophen-2-yl-acetyl)-piperazin-1-yl]-ethylcarbamoyl}-ethylcarbamoyl)-cyclopentyl]-amide Analogously to Example 95) 4-[2-2(R)-amino-3-phenyl-propionylamino)-ethyl]-piperazine-1-carboxylic acid tert-butyl ester (obtained starting from Z-D-phenylalanine and N-Boc-4-hydroxyethylpiperazine by reactions and couplings widely described in literature and in part already reported in previous examples) (100 mg, 0.26 mmol) and 2-benzo[b]thiophen-2-yl-3-oxa-1-azaspiro[4.4]-non-1-en-4-one (72 mg, 0.26 mmol) are caused to react in DMF to yield a product which is deprotected and subsequently acylated with thiophen-2-yl-acetyl chloride in CH$_2$Cl$_2$ (as described in Example 94 and purified by flash chromatography using AcOEt as the eluent. 69 mg (0.10 mmol) of benzo[b]thiophene-2-carboxylic acid [1-(2-phenyl-1(R)-{2-[4-(thiophen-2-yl-acetyl)-piperazin-1-yl]-ethylcarbamoyl}-ethylcarbamoyl)-cyclopentyl]-amide are so obtained.

MS (m/z): 672.3 (MH$^+$). HPLC (method A): Rt=3.87 min.

EXAMPLE 101

Benzo[b]thiophene-2-carboxylic acid [1-(2-phenyl-1(R)-{2-[4-(tetrahydro-pyran-4-ylmethyl)-piperazin-1-yl]-ethylcarbamoyl}-ethylcarbamoyl)-cyclopentyl)-amide TFA salt The compound of the title is obtained by a procedure analogous to that described in Example 100, but carrying out a reductive amination with tetrahydropyranyl 4-carboxyaldehyde in place of an acylation step with thiophen-2-yl-acetyl chloride.

MS (m/z): 646.2 (MH$^+$). HPLC (method A): Rt=3.24 min.

EXAMPLE 102

5-Chloro-benzofuran-2-carboxylic acid {1-[1R-(3-morpholin-4-yl-propylcarbamoyl)-2-phenyl-ethylcarbamoyl]-cyclopentyl}-amide 196 mg of 5-chlorobenzofuran-2-carboxylic acid are suspended in 12 ml of anhydrous CH$_2$Cl$_2$, in nitrogen atmosphere. 100 µl of oxalyl chloride and one drop of DMF are then added. The stirring is maintained until the reaction is finished. The solvent is then evaporated and the residue is brought to dryness in a hard vacuum. 87 mg of the so obtained acylic chloride are added to a mixture of 132 mg of 1-amino-cyclopentanecarboxylic acid [1(R)-(3-morpholin-4-yl-propylcarbamoyl)-2-phenyl-ethyl]-amide bis-hydrochloride, 200 µl of TEA and 10 ml of anhydrous CH$_2$Cl$_2$ under magnetic stirring. Once the reaction is over, the solvent is evaporated and the residue is dissolved with a mixture of ethyl acetate and K$_2$CO$_3$ aq. 10%, by vigorously stirring. After separation of the organic phase, washings with basic water, drying on anhydrous Na$_2$SO$_4$, filtration and evaporation of the solvent, 134 mg of a residue are obtained, which are then purified by flash chromatography, eluting with increasing amounts of methanol in ethyl acetate until MeOH/AcOH=1/6 v/v, so to obtain the desired amide.

MS (m/z): 581.3 (MH$^+$). HPLC (method C): Rt=13.14 min.

With analogous procedure the following compounds have been prepared:

EXAMPLE 103

5-Chloro-benzo[b]thiophene-2-carboxylic acid {1-[1R-(3-morpholin-4-yl-propylcarbamoyl)-2-phenyl-ethylcarbamoyl-cyclopentyl}-amide MS (m/z): 597.3 (M+H$^+$). HPLC (method C): Rt=13.80 min.

EXAMPLE 104

5-Bromo-benzofuran-2-carboxylic acid {1-[1R-(3-morpholin-4-yl-propylcarbamoyl)$_2$-phenyl-ethylcarbamoyl]-cyclopentyl}-amide MS m/z: 625.2 (M+H$^+$, monoisotopic). HPLC (method C): Rt=13.41 min.

EXAMPLE 105

6-Chloro-benzo[b]thiophene-2-carboxylic acid {1-[1R-(3-morpholin-4-yl-propylcarbamoyl)-2-phenyl-ethylcarbamoyl]-cyclopentyl}-amide MS m/z: 597.3 (N+H$^+$). HPLC (method C): Rt=13.58 min.

EXAMPLE 106

6-Methoxy-benzo[b]thiophene-2-carboxylic acid {1-[1R-(3-morpholin-4-yl-propylcarbamoyl)-2-phenyl-ethylcarbamoyl]-cyclopentyl}-amide MS m/z: 593.3 (M+H$^+$). HPLC (method C): Rt=12.62 min.

EXAMPLE 107

4-Chloro-benzo[b]thiophene-2-carboxylic acid {1-[1R-(3-morpholin-4-yl-propylcarbamoyl)-2-phenyl-ethylcarbamoyl]-cyclopentyl}-amide MS m/z: 597.3 (M+H$^+$). HPLC (method C): Rt=13.79 min.

EXAMPLE 108

6-Bromo-benzo[b]thiophene-2-carboxylic acid {1-[1R-(3-morpholin-4-yl-propylcarbamoyl)-2-phenyl-ethylcarbamoyl]-cyclopentyl}-amide MS m/z: 641.3 (M+H$^+$, monoisotopic). HPLC (method C): Rt=13.86 min.

EXAMPLE 109

6-Bromo-benzo[b]thiophene-2-carboxylic acid {1-[1R-(3-morpholin-4-yl-propylcarbamoyl)-2-phenyl-ethylcarbamoyl]-cyclohexyl}-amide MS m/z: 655.2 (M+H$^+$, monoisotopic). HPLC (method C): Rt=14.63 min.

EXAMPLE 110

5-Fluoro-1-methyl-1H-indole-2-carboxylic acid {1-[1R-(3-morpholin-4-yl-propylcarbamoyl)-2-phenyl-ethylcarbamoyl]-cyclopentyl}-amide MS m/z: 578.3 (M+H$^+$). HPLC (method C): Rt=13.18 min.

EXAMPLE 111

6-Chloro-1-methyl-1H-indole-2-carboxylic acid {1-[1R-(3-morpholin-4-yl-propylcarbamoyl)-2-phenyl-ethylcarbamoyl]-cyclopentyl}-amide MS m/z: 594.3 (M+H$^+$). HPLC (method C): Rt=14.03 min.

EXAMPLE 112

7-Methyl-benzo[b]thiophene-2-carboxylic acid {1-[1R-(3-morpholin-4-yl-propylcarbamoyl)-2-phenyl-ethylcarbamoyl]-cyclopentyl}-amide MS m/z: 577.3 (M+H$^+$). HPLC (method C): Rt=13.26 min.

EXAMPLE 113

5-Methyl-benzofuran-2-carboxylic acid {1-[1R-(3-morpholin-4-yl-propylcarbamoyl)-2-phenyl-ethylcarbamoyl]-cyclopentyl}-amide MS m/z: 561.3 (M+H$^+$). HPLC (method C): Rt=13.01 min.

EXAMPLE 114

1,5-Dimethyl-1H-indole-2-carboxylic acid {1-[1R-(3-morpholinyl-propylcarbamoyl)-2-phenyl-ethylcarbamoyl]-cyclopentyl}-amide MS m/z: 574.3 (M+H$^+$). HPLC (method D): Rt=13.62 min.

EXAMPLE 115

6-Amino-benzo[b]thiophene-2-carboxylic acid {1-[1R-(3-morpholin-4-yl -propylcarbamoyl)-2-phenyl-ethylcarbamoyl]-cyclopentyl]-amide MS m/z: 578.2 (M+H$^+$). HPLC (method D): Rt=8.62 min.

EXAMPLE 116

6,7-Dichloro-benzo[b]thiophene-2-carboxylic acid {1-[1R-(3-morpholin-4-yl-propylcarbamoyl)-2-phenyl-ethylcarbamoyl]-cyclopentyl}-amide MS m/z: 631.3 (M+H$^+$). HPLC (method C): Rt=14.57 min.

EXAMPLE 117

6-Iodo-naphthalene-2-carboxylic acid (1-(2-phenyl-1R-{[1-(tetrahydro-pyran-4-ylmethyl)-piperidin-4-ylmethyl]-carbamoyl}-ethylcarbamoyl)-cyclopentyl]-amide 118a) 18.0 g of 4-tetrahydropyrancarboxylic acid are introduced in a 250 ml flask with a calcium chloride tube, and dissolved in 130 ml of CH$_2$Cl$_2$. Under magnetic stirring, 15 ml of oxalyl chloride and 3 drops of DMF are added successively. The solution, that regularly degasses, is kept under magnetic stirring for 16 hours. After evaporation of the solvent, the residue is dried in hard vacuum at room temperature, dissolved in 100 ml of CH$_2$Cl$_2$ and put in a bath of ice and water, maintaining a vigorous magnetic stirring. A solution of 21.75 g of ethyl 4-piperidincarboxylate in 30 ml of CH$_2$Cl$_2$ containing 15.35 g of TEA is added to the mixture by means of a dripping funnel. During the addition, that lasts 3 hours, a clear suspension forms. The reaction mixture is left to stand overnight, then CH$_2$Cl$_2$ is evaporated and the residue is brought to dryness in hard vacuum. The residue is dissolved in 110 ml of ammonia aq. 25%, then methanol is added until complete solubilisation. Methanol is refluxed until the ester disappears (samples are taken, evaporated and analised by 1H-NMR). The solution is brought to small volume and extracted 25 times with 100 ml of chloroform to give, after evaporation of the solvent, 21.4 g of raw diamide.

14.79 g of the so obtained diamide are added in portions to 175 ml of a solution 1M of borane in THF. The addition lasts about 1 hour and it is carried out under a nitrogen flow, so that the temperature does not exceed 35° C. Once the addition is completed, the reaction mixture is heated to reflux and the reflux is maintained for 11 hours. In a bath of ice and water, 130 ml of a solution 4M of HCl in 1,4-dioxane, previously diluted with 100 ml of methanol, are added drop by drop to the solution obtained as above. The reaction mixture is heated to reflux, and the reflux is maintained for 12 hours before cooling at 0–4° C.

By filtration 7.95 g of C-[1-(tetrahydro-pyran-4-ylmethyl)-piperidin-4-yl]-methylamine bis-hydrochloride are recovered. From mother liquor, by dilution to doubled volume with diethyl ether, further 1.85 g of the desired product are recovered.

1H-NMR (200 MHz, DMSO-d$_6$), • (ppm): 1.09–1.33 (m, 2H); 1.51–2.20 (m, 8H); 2.59–3.08 (m, 6H); 3.09–3.58 (m, 4H); 3.76–3.91 (m, 2H); 8.18 (br, 3H); 10.20 (br, 1H).

Analogously, the following amines have also been prepared:

C-[1-(4-Methyl-tetrahydro-pyran-4-ylmethyl)-piperidin-4-yl]-methylamine

MS (m/z): 227.2 (MH$^+$) $^1$H NMR (200 MHz): (δ, CDCl$_3$) 0.94 (s, 3H); 1.08–1.69 (m, 9H); 2.10 (s, 2H); 2.10–2.30 (m, 2H); 2.48–2.59 (m, 2H); 2.67–2.83 (m, 2H); 3.47–3.79 (m, 4H). C-[4-Methyl-1-(4-methyl-tetrahydro-pyran-4-ylmethyl)-piperidin-4-yl]-methylamine MS (m/z): 227.3 (MH$^+$)

C-[4-Methyl-1-(tetrahydro-pyran-4-ylmethyl)-piperidin-4-yl]-methylamine

MS (m/z): 241.2 (MH$^+$)

117b) Staring from the amine obtained in Example 117a), by a peptidic synthesis using Boc, under the operative conditions well known to a skilled person, by reacting the above said amine with Boc-D-phenylalanine O-succinimidoester, deprotecting, reacting with N-Boc 1-amino-1-cyclopentancarboxylic acid and deprotecting, the compound 1-amino-cyclopentanecarboxylic acid (2-phenyl-1R-{[1-(tetrahydropyran-4-ylmethyl)-piperidin-4-ylmethyl]-carbamoyl}-ethyl)amide is obtained This compound is caused to react with the chloride of 6-iodonaphthalen-2-carboxylic acid, by a procedure analogous to that described in Example 102), thus obtaining the final product &iodo-naphthalene-2-carboxylic acid [1-(2-phenyl-1R-{[1-(tetrahydropyran-4-ylmethyl)-piperidin-4-ylmethyl]-carbamoyl}-ethylcarbamoyl)-cyclopentyl]-amide.

MS m/z: 751.3 (M+H$^+$). HPLC (method D): Rt=14.00 min.

Analogously to that described in Example 117), by reaction of the corresponding carboxylic acids activated with 1-amino-cyclopentanecarboxylic acid (2-phenyl-1R-{[1-(tetrahydro-pyran-4-ylmethyl)-piperidin-4-ylmethyl]-carbamoyl}-ethyl)-amide, the following compounds have been obtained:

EXAMPLE 118

6-Methoxy-naphthalene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 655.2 (M+H$^+$). HPLC (method D): Rt=12.42 min. 1H-NMR (DMSO-d$_6$). δ (amongst the others): 0.94–1.07 (m, 4H); 1.42–1.72 (m, 12H); 1.74–1.81 (m, 1H); 1.89–2.00 (m, 3H); 2.24–2.33 (m, 1H); 2.55–2.63 (m, 2H); 2.82–2.90 (m, 2H); 2.94–3.01 (m, 1H); 3.74–3.83 (m, 2H); 3.91 (s, 3H); 4.42–4.49 (m, 1H); 7.10–7.21 (m, 5H); 7.23–7.27 (m, 1H); 7.38–7.41 (m, 1H); 7.51 (t, J=5.7 Hz, 1H); 7.79 (d, J=8.6, 1H); 7.86–7.97 (m, 3H); 8.45 (s, 1H); 8.69 (s, 1H).

EXAMPLE 119

6-Bromo-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)cyclopentyl]-amide MS m/z: 693.5 (M+H$^+$, monoisotopic). HPLC (method D): Rt=13.18 min. 1H-NMR (DMSO-d$_6$). δ(amongst the others): 0.97–1.12 (m, 4H); 1.39–1.73 (m, 12H); 1.74–1.81 (m, 1H); 1.89–1.96 (in, 1H); 1.97–2.04 (m, 2H); 2.21–2.29 (m, 1H); 2.63–2.71 (m, 2H); 2.79–2.92 (m, 2H); 2.95–3.03 (m, 1H); 3.77–3.85 (m, 2H); 4.40–4.48 (m, 1H); 7.10–7.22 (m, 5H); 7.45 (t, J=5.7 Hz, 1H); 7.54 (dd, J=1.7 and 8.4 Hz, 1H); 7.67 (d, J=0.8 Hz, 1H) 7.79 (d, J 8.4, 1H); 7.85 (d, J=8.6 Hz, 1H); 7.95 (s,br, 1H); 8.85 (s, 1H).

EXAMPLE 120

6-Chloro-benzofuran-2-carboxylic acid [1-(2-phenyl-1R-{[1-(tetrahydro-pyran-4-ylmethyl)-piperidin-4-ylmethyl]-carbamoyl-3-ethylcarbamoyl)-cyclopentyl]-amide MS m/z: 649.3 (M+H$^+$). HPLC (method D): Rt=13.00 min. 1H-NMR (DMSO-d$_6$). • (amongst the others): 0.97–1.12 (m, 4H); 1.42–1.73 (m, 12H); 1.74–1.81 (m,1H); 1.89–1.96 (m, 1H); 1.97–2.04 (m, 2H); 2.212.29 (m, 1H); 2.63–2.71 (m, 2H); 2.79–2.92 (m, 2H); 2.95–3.03 (m, 1H); 3.77–3.85 (m, 2H); 4.40–4.48 (m, 1H); 7.10–7.22 (m, 5H); 7.42 (dd, J=1.8 and 8.4 Hz, 1H); 7.46 (t, J=5.8 Hz, 1H); 7.66 (d, J=0.9 Hz, 1H) 7.81–7.86 (m, 21H); 8.84 (s, 1H).

EXAMPLE 121

5-Fluoro-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 633.5 (M+H$^+$). HPLC (method D): Rt=12.10 min. 1H-NMR (DMSO-d$_6$).• (amongst the others): 0.97–1.12 (m, 4H); 1.42–1.73 (m, 12H); 1.74–1.81 (m, 1H); 1.89–1.96 (m, 1H); 1.97–2.04 (m, 2H); 2.21–2.29 (m, 1H); 2.63–2.71 (m, 2H); 2.78–2.93 (m, 2H); 2.95–3.03 (m, 1H); 3.75–3.85 (m, 2H); 4.40–4.48 (m, 1H); 7.10–7.22 (m, 5H);

7.32–7.37 (m, 1H); 7.46 (t, J=5.8 Hz, 1H); 7.60–7.66 (m, 2H); 7.71 (dd, J=4.1 and 9.0 Hz, 1H) 7.83 (d, J=8.6 Hz, 1H); 8.84 (s, 1H).

EXAMPLE 122

5-Chloro-benzofuran-2-carboxylic acid [1-(2-phenyl-1R-{[1-(tetrahydro-pyran-4 ylmethyl)-piperidin-4-ylmethyl]-carbamoyl}-ethylcarbamoyl)cyclopentyl]-amide MS m/z: 649.5 (M+H$^+$). HPLC (method D): Rt=12.78 min. 1H-NMR (DMSO-d6). • (amongst the others): 0.97–1.12 (m, 4H); 1.42–1.73 (m, 12H); 1.74–1.81 (m, 1H); 1.89–1.96 (m, 1H); 1.97–2.04 (m, 2H); 2.21–2.29 (m, 1H); 2.63–2.71 (m, 2H); 2.78–2.93 (m, 2H); 2.95–3.03 (m, 1H); 3.75–3.85 (m, 2H); 4.40–4.48 (m, 1H); 7.10–7.22 (m, 5H); 7.46 (t, J=5.8 Hz, 1H); 7.50–7.53 (m, 1H); 7.61 (s, br, 1H); 7.71 (d, J=8.8 Hz, 1H) 7.85 (d, J=8.6 Hz, 1H); 7.92 (d, J=2.2, 11H); 8.87 (s, 1H).

EXAMPLE 123

5-Bromo-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)cyclopentyl]-amide MS m/z: 693.5 (M+H$^+$, monoisotopic). HPLC (method D): Rt=13.14 ml. 1H-NMR (DMSO-d6). • (amongst the others): 0.97–1.12 (m, 4H); 1.42–1.73 (m, 12H); 1.74–1.81 (m, 1H); 1.89–1.96 (m, 1H); 1.97–2.04 (m, 2H); 2.21–2.29 (m, 1H); 2.63–2.71 (m, 2H); 2.78–2.93 (m, 2H); 2.95–3.03 (m, 1H); 3.75–3.84 (m, 2H); 4.40–4.48 (m, 1H); 7.11–7.21 (m, 5H); 7.44 (t, J=5.8 Hz, 1H); 7.58–7.69 (m, 3H) 7.85 (d, J=8.6 Hz, 1H); 8.06 (d, J=2.0, 1H); 8.87 (s, 1H).

EXAMPLE 124

7-tert-Butyl-benzofuran-2-carboxylic acid [1-(2-phenyl-1R-{[1-(tetrahydro-pyran-4 ylmethyl)-piperidin-4-ylmethyl]-carbamoyl}-ethylcarbamoyl)-cyclopentyl]-amide MS m/z: 671.6 (M+H$^+$). HPLC (method D): Rt=15.16 min.

EXAMPLE 125

6-Methyl-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 629.5 (M+H$^+$). HPLC (method D): Rt=12.69 min.

EXAMPLE 126

5-Methyl-benzofuran-2-carboxylic acid [1-(2-phenyl-1R-([1-(tetrahydro-pyran-4-ylmethyl)-piperidin-4-ylmethyl]-carbamoyl}-ethylcarbamoyl)-cyclopentyl]-amide MS m/z: 629.5 (M+H$^+$). HPLC (method D): Rt=12.66 min. 1H-NMR (DMSO-d$_6$). • (amongst the others): 0.97–1.12 (m, 4H); 1.42–1.73 (m, 12H); 1.74–1.81 (m, 1H); 1.89–1.96 (m, 1H); 1.97–2.04 (m, 2H); 2.21–2.29 (m, 1H); 2.44 (s, 3H) 2.63–2.71 (m, 2H); 2.78–2.93 (m, 2H); 2.95–3.03 (m, 1H); 3.75–3.84 (m, 2H); 4.40–4.48 (m, 1H); 7.11–7.21 (m, 5H); 7.29–7.33 (m, 1H) 7.49 (t, J=5.7 Hz, 1H); 7.53–7.60 (m, 3H); 7.86 (d, J=8.5 Hz, 1H); 8.76 (s, 1H).

EXAMPLE 127

5-Iodo-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 741.5 (M+H$^+$). HPLC (method D): Rt=13.42 min. 1H-NMR (DMSO-d6). • (amongst the others): 0.97–1.12 (m, 4H); 1.42–1.73 (m, 12H); 1.741.81 (m, 1H); 1.89–1.96 (m, 1H); 1.97–2.04 (m, 214); 2.21–2.29 (m, 1H); 2.63–2.71 (m, 2H); 2.78–2.93 (m, 2H); 2.95–3.03 (m, 1H); 3.75–3.84 (m, 2H); 4.40–4.48 (m, 1H); 7.11–7.21 (m, 5H); 7.43 (t, J=5.8 Hz, 1H); 7.53 (d, J=8.7 Hz, 111) 7.58 (s, 1H); 7.76 (dd, J=1.8 and 8.7 Hz, 1H); 7.86 (d, J=8.6 Hz, 1H); 8.22 (d, J=1.7, 11H); 8.88 (s, 1H).

EXAMPLE 128

5-tert-Butyl-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 671.5 (M+H$^+$). HPLC (method D): Rt=14.90 min.

EXAMPLE 129

6-Iodo-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 757.2 (M+H$^+$). HPLC (method D): Rt=13.85 min.

EXAMPLE 130

6-Chloro-benzo[b]thiophene-2-carboxylic acid [1-(2-phenyl-1R-{[1-(tetrahydro-pyran-4-ylmethyl)-piperidin-4-ylmethyl]-carbamoyl)-ethylcarbamoyl)-cyclopentyl]-amide MS m/z: 665.4 (M+H$^+$). HPLC (method D): Rt=13.32 min. 1H-NMR (DMSO-d6). • (amongst the others): 0.97–1.12 (m, 4H); 1.42–1.73 (m, 12H); 1.74–1.81 (m, 1H); 1.87–1.94 (m, 1H); 2.17–2.28 (m, 1H); 2.65–2.71 (m, 2H); 2.79–2.87 (m, 1H); 2.88–2.99 (m, 2H); 3.31–3.20 (m, 1H); 3.76–3.84 (m, 2H); 4.42–4.49 (n, 1H); 7.10–7.21 (m, 5H); 7.44 (t, J=5.8 Hz, 1H); 7.49 (dd, J=2.0 and 8.5, 1H), 7.85 (d, J=8.6 Hz, 1H); 8.00 (d, J=8.5 Hz, 1H); 8.22 (d, J=1.9 Hz, i); 8.28 (s, 1H); 8.93 (s, 1H).

EXAMPLE 131

7-Bromo-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 709.4 (M+H$^+$, monoisotopic). HPLC (method D): Rt=13.12 min.

EXAMPLE 132

7-Iodo-benzo[b]thiophene-2-carboxylic acid [1-(2-phenyl-1R-{[1-(tetrahydro-pyran 4-ylmethyl)-piperidin-4-ylmethyl]-carbamoyl}-ethylcarbamoyl)-cyclopentyl]-amide MS m/z: 757.4 (M+H$^+$). HPLC (method D): Rt=13.38 min.

EXAMPLE 133

6-Trifluoromethyl-benzo[b]thiophene-2-carboxylic acid [1-(2-phenyl-1R-{[1-tetrahydro-pyran-4-ylmethyl)-piperidin-4-ylmethyl]-carbamoyl}-ethylcarbamoyl)-cyclopentyl]-amide MS m/z: 699.5 (M+H$^+$). HPLC (method D): Rt=13.88 min.

EXAMPLE 134

7-Methyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 645.5 (M+H$^+$). HPLC (method D): Rt=12.83 min 1H-NMR (DMSO-d6). • (amongst the others): 0.98–1.12 (m, 4H); 1.36–1.82 (m, 14H); 1.87–1.95 (m, 1H); 1.95–2.06 (m, 2H); 2.19–2.29 (m, 1H); 2.53 (s, 3H); 2.67–2.74 (m, 2H); 2.80–2.94 (m, 2H); 3.15–3.28 (m, 3H); 3.76–3.83 (m, 2H); 4.41–4.48 (m, 1H); 7.10–7.23 (m, 5H); 7.29–7.33 (m, 1H); 7.37–7.41 (m, 1H); 7.44 (t, J=5.7 Hz, 1H); 7.86–7.83 (m, 1H); 7.86 (d, J=8.6 Hz, 1H); 8.31 (s, 1H); 8.86 (s, 1H).

EXAMPLE 135

6-Methoxy-benzo[b]thiophene-7-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 661.5 (M+H$^+$). HPLC (method D): Rt=12.32 min.

EXAMPLE 136

7-Trifluoromethyl-benzo[b]thiophene-2-carboxylic acid [1-(2-phenyl-1R-{[1-(tetrahydro-pyran-4-ylmethyl)piperidin-4-ylmethyl]-carbamoyl}-ethylcarbamoyl)-cyclopentyl]-amide MS m/z: 699.5 (M+H$^+$). HPLC (method D): Rt=13.31 min.

EXAMPLE 137

7-Chloro-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 665.4 (M+H$^+$). HPLC (method D): Rt=12.99 min.

EXAMPLE 138

5-Methyl-benzo[b]thiophene-2-carboxylic acid [1-(2-phenyl-1R-{[1-(tetrahydro-pyran-4-ylmethyl)piperidin-ylmethyl]-carbamoyl}-ethylcarbamoyl)-cyclopentyl]-amide MS m/z: 645.5 (M+H$^+$). HPLC (method D): Rt=13.03 min. 1H-NMR (DMSO-d6). • (amongst the others): 1.00–1.11 (m, 4H); 1.43–1.80 (m, 13H); 1.87–1.94 (m, 1H); 1.95–2.04 (m, 2H); 2.18–2.28 (m, 1H); 2.44 (s, 3H); 2.66–2.73 (m, 2H); 2.80–2.87 (m, 1H); 2.90–3.00 (m, 2H); 3.14–3.27 (m, 3H); 3.75–3.84 (m, 2H); 4.41–4.50 (m, 1H); 7.10–7.21 (m, 5H); 7.29–7.33 (m, 1H); 7.47 (t, J=5.8 Hz, 1H); 7.75 (s, 1H); 7.84 (d, J=8.6 Hz, 1H); 7.87–7.91 (m, 1H); 8.19 (s, 1H); 8.83 (s, 1H).

EXAMPLE 139

6-Methyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 645.5 (M+H$^+$). HPLC (method D): Rt=13.02 min. 1H-NMR (DMSO-d6). • (amongst the others): 0.97–1.12 (m, 4H); 1.42–1.73 (m, 12H); 1.74–1.81 (m, 1H); 1.87–1.94 (m, 1H); 2.17–2.28 (m, 1H); 2.45 (s, 3H); 2.67–2.73 (m, 2H); 2.79–2.87 (m, 1H); 2.88–2.99 (m, 2H); 3.31–3.20 (m, 1H); 3.76–3.84 (m, 2H); 4.42–4.49 (m, 1H); 7.10–7.21 (m, 5H); 7.28 (d, J=8.2 Hz, 1H); 7.47 (t, J=5.6 Hz, 1H); 7.78–7.88 (m, 3H); 8.22 (d, J=1.9 Hz, 1H); 8.22 (s, 1H); 8.80 (s, 1H).

EXAMPLE 140

Benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide

EXAMPLE 141

6-Fluoro-benzo[b]thiophene-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide MS m/z: 649.3 (M+H$^+$). HPLC (method D): Rt=12.51 min. 1H-NMR (DMSO-d6). • (amongst the others): 0.97–1.12 (m, 4H); 1.42–1.73 (m, 12H); 1.74–1.81 (m, 1H); 1.87–1.94 (m, 1H); 2.17–2.28 (m, 1H); 2.45 (s, 3H); 2.67–2.73 (m, 2H); 2.79–2.87 (m, 1H); 2.88–3.00 (m, 2H); 3.31–3.20 (m, 1H); 3.76–3.84 (m, 2H); 4.42–4.49 (in, 1H); 7.10–7.21 (m, 5H); 7.34 (m, 1H); 7.47 (t, J=5.8 Hz, 1H); 7.84 (d, J=8.6, 1H); 7.95–7.98 (m, 1H); 8.00–8.04 (m, 1H); 8.27 (s, 1H); 8.89 (s, 1H).

EXAMPLE 142

1-Methyl-1H-indole-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide

EXAMPLE 143

7-Chloro-1-methyl-1H-indole-2-carboxylic acid [1R-(2-phenyl-1-{[1-(tetrahydro-pyran-4-ylmethyl)piperidin-4-ylmethyl]-carbamoyl}-ethylcarbamoyl)-cyclopentyl]-amide

EXAMPLE 144

5-Chloro-3-methyl-benzofuran-2-carboxylic acid [1R-(2-phenyl-1-{[1-(tetrahydro-pyran-4-ylmethyl)-piperidin-4-ylmethyl]-carbamoyl}-ethylcarbamoyl)-cyclopentyl]-amide

EXAMPLE 145

6-Diethylamino-benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide MS m/z: 686.4 (M+H$^+$). HPLC (method D): Rt=8.76 min.

EXAMPLE 146

5-Methoxy-benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide MS m/z: 645.5 (M+H$^+$). HPLC (method D): Rt=11.98 min.

EXAMPLE 147

5-Diethylamino-benzofuran-2-carboxylic acid [1-(2-phenyl-1-{1R-(tetrahydro-pyran-4-ylmethyl)-piperidin-4-ylmethyl]-carbamoyl}-ethylcarbamoyl)-cyclopentyl]-amide MS m/z: 686.6 (M+H$^+$). HPLC (method D): Rt=8.58 min.

EXAMPLE 148

3,5,6-Trimethyl-benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide

EXAMPLE 149

Naphthalene-2-carboxylic acid [1-(2-phenyl-1-{[1R-(tetrahydro-pyran-4-ylmethyl)-piperidin-4ylmethyl]-carbamoyl}-ethylcarbamoyl)-cyclopentyl]-amide MS m/z: 639.5 (M+H$^+$). HPLC (method D): Rt=13.14 min.

EXAMPLE 150

5-Bromo-naphthalene-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide MS m/z: 703.4 (M+H$^+$, monoisotopic). HPLC (method D): Rt=13.53 in.

EXAMPLE 151

Naphthalene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide MS m/z: 625.5 (M+H$^+$). HPLC (method D) Rt=12.29 min. 1H-NMR (DMSO-d6). δ (amongst the others): 0.94–1.07 (m, 4H); 1.43–1.72 (m, 12H); 1.76–1.83 (m, 1H); 1.90–2.00 (m, 3H); 2.25–2.34 (m, 1H); 2.55–2.63 (m, 2H); 2.82–2.90 (m, 2H); 2.94–3.01 (m, 1H); 3.74–3.83 (m, 2H); 3.91 (s, 3H); 4.42–4.49 (m, 1H); 7.10–7.21 (m, 5H); 7.23–7.27 (m, 1H); 7.52 (t, J=5.7 Hz, 1H); 7.58–7.67 (m, 2H); 7.80 (d, J=8.6, 1H); 7.95–8.06 (m, 41); 8.53 (s, 1H); 8.78 (s, 1H).

By analogous procedure to that described in Example 117, the following compounds have moreover been prepared:

EXAMPLE 152

Benzo[b]thiophene-2-carboxylic acid [1-(2-phenyl-1(R)-{[1-(tetrahydro-pyran-4-ylmethyl)-azetidin-3-ylmethyl]-carbamoyl}-ethylcarbamoyl)-cyclopentyl]-amide, by using ethyl 3-azetidincarboxylate in place of ethyl 4-piperidincarboxylate MS (m/z): 603.3 (MH$^+$). HPLC (method A): Rt=3.63 min.

EXAMPLE 153

6-Bromo-naphthalene-2-carboxylic acid [1-(1(R)-{([1-(4-methyl-tetrahydro-pyran-4-ylmethyl)-piperidin-4-ylmethyl]-carbamoyl}-2-phenyl-ethylcarbamoyl)-cyclopentyl]-amide, by using C-[1-(4-Methyl-tetrahydro-pyran-4-ylmethyl)-piperidin-4-yl]-methylamine prepared as described in Example 117a)

MS (m/z): 617.4 (MH$^+$, isotopic pattern of Br). HPLC (method A): Rt=4.01 min.

EXAMPLE 154

6-Bromo-naphthalene-2-carboxylic acid [1-(1(R)-{[1-(5-ethyl-[1,3]dioxan-5-ylmethyl)-piperidin-4-ylmethyl]-carbamoyl}-2-phenyl-ethylcarbamoyl)-cyclopentyl]-amide, by using 5-ethyl-[1,3]dioxane-5 carboxylic acid in place of 4-tetrahydropyrancarboxylic acid

EXAMPLE 155

6-Bromo-naphthalene-2-carboxylic acid [1-(1(R)-{[4-methyl-1-(4-methyl-tetrahydro-pyran-4-ylmethyl)-piperidin-4-ylmethyl]-carbamoyl}-2-phenyl-ethylcarbamoyl)-cyclopentyl]-amide, by using C-[4-methyl-1-(4-methyl-tetrahydro-pyran-4-ylmethyl)-piperidin-4-yl]-methylamine prepared as described in Example 117a)

EXAMPLE 156

6-Bromo-naphthalene-2-carboxylic acid [1-((R)-{[4-methyl-1-(tetrahydro-pyran-4-ylmethyl)-piperidin-4-ylmethyl]-carbamoyl}-2-phenyl-ethylcarbamoyl)-cyclopentyl]-amide, by using C-[4-methyl-1-(tetrahydro-pyran-4-ylmethyl)-piperidin-4-yl]-methylamine prepared as described in Example 117a)

MS (m/z): 717.4 (MH$^+$, isotopic pattern of Br). HPLC (method A): Rt=4.16 min.

HPLC methods

Mobile phase: A=H$_2$O+0.1% TFA; B=MeCN+0.1% TFA

METHOD A
Column: Zorbax™ SB-18, 3.5 μm, 100 Å(50×4.6 mm)
Gradient: from A/B=9515 to A/B=5/95 in 6.5 min+1 min isocratic
Flow rate: 3 ml/min
λ=220, 270 nm.

METHOD B
Column: Platinum™ RP-18, 3 μm, 100 Å(33×7 mm)
Gradient: from A/B=95/5 to A/B=5/95 in 6.5 min+1 min isocratic
Flow rate: 3 ml/min
λ=220, 270 nm.

METHOD C
Column: Jupiter™ C18, 5 μm (250×4.6 mm)
Gradient: from A/B=85/15 to A/B=5/95 in 20 min
Flow rate: 1 ml/min
λ=210 nm.

METHOD D
Column: Symmetry™ 300 C18, 5 μm (250×4.6 mm)
Gradient: from A/B=85/15 to A/B=5/95 in 20 mil
Flow rate: 1 ml/min
λ=210 mm.

METHOD E
Column: Protein & Peptide Vydac™ C18 (250×4.6 mm)
Gradient: from A/B=80/20 to A/B=20/80 in 25 min+A/B=20/80 for 10 min
Flow rate: 1 ml/min
λ=230 nm.

METHOD F
Column: Inertsil ODS-3 (GL Sciences), 3 μm (50×3 mm) (250×4.6 mm)
Gradient: from A/B=80/20 to A/B=30/70 in 9 min
Flow rate: 0.8 ml/min
λ=230 $_1$ nm.

List of Abbreviations

In the present description the following abbreviations have been used:

Ac5c, aminocyclopentanecarboxylic;Ac6c, aminocyclohexanecarboxylic; AcOEt, ethyl acetate; Boc, N-tert-butyloxycarbonyl;BSA,N,O-bis(trimethylsilyl)acetamide; DCM, dichloromethane; DIPEA, N,N-diisopropylethylamine; DMF, N,N-dimethylformamide; EDC, 1-ethyl-3-(3-dimethylaminopropyl)carbodiimide hydrochloride; EtOAc, ethyl acetate; HOBt, 1-hydroxybenzotriazole; TEA, triethylamine; TEMPO, 2,2,6,6-tetramethyl-1-piperidinyloxy; TFA, trifluoroacetic acid; THF, tetrahydrofuran; TMSCl, trimethylsilylchloride; Z, N-benzyloxycarbonyl.

The evaluation of the antagonist activity on NK-2 receptors has been assessed by binding and functional tests according to that already described in literature in relation to NK-2 antagonists.

In particular, the affinity of the present compounds for the human NK-2 receptor has been assessed by a binding test using Chinese hamster ovary (CHO) cell membranes transfected with NK-2 receptor of human ileum together with [$^{125}$I]NKA (Amersham, aspecific activity 2000 Ci/mmol) radiobinder at the concentration of 100 pM in competition studies.

The test substances have been tested within a concentration range from 0.01 nM to 10 nM. At the end of the incubation time (30 min, 20° C.) the samples have been filtered and radioactivity has been determined using a gamma-counter.

The data shown in the following Table I have been obtained for some compounds of general formula (I) and refer to the affinity values of human NK-2 receptor:

TABLE I

| Compound | pKi | Compound | pKi |
|---|---|---|---|
| Example 1 | 9.2 | Example 2 | 9.8 |
| Example 3 | 9.6 | Example 4 | 9.8 |
| Example 5 | 9.7 | Example 6 | 9.7 |
| Example 7 | 9.9 | Example 8 | 9.6 |
| Example 9 | 8.8 | Example 10 | 9.3 |
| Example 11 | 8.7 | Example 12 | 9.5 |
| Example 13 | 9.0 | Example 14 | 9.9 |
| Example 15 | 10.0 | Example 16 | 9.3 |
| Example 17 | 8.6 | Example 18 | 9.1 |
| Example 19 | 8.9 | Example 20 | 9.1 |
| Example 21 | 9.6 | Example 22 | 9.2 |
| Example 23 | 8.7 | Example 24 | 9.1 |
| Example 25 | 9.6 | Example 26 | 10.3 |
| Example 27 | 10.2 | Example 28 | 10.3 |
| Example 30 | 10.0 | Example 31 | 10.1 |
| Example 32 | 8.9 | Example 33 | 9.2 |
| Example 34 | 8.9 | Example 36 | 10.6 |
| Example 37 | 10.9 | Example 38 | 9.5 |
| Example 40 | 8.9 | Example 41 | 8.8 |
| Example 42 | 8.3 | Example 44 | 9.1 |
| Example 45 | 8.3 | Example 47 | 8.6 |
| Example 48 | 9.4 | Example 49 | 8.6 |
| Example 50 | 9.4 | Example 51 | 9.1 |
| Example 52 | 8.7 | Example 53 | 8.6 |
| Example 54 | 8.5 | Example 55 | 9.0 |
| Example 56 | 8.8 | Example 57 | 9.9 |
| Example 58 | 8.5 | Example 60 | 9.0 |
| Example 61 | 9.0 | Example 62 | 8.7 |
| Example 63 | 9.2 | Example 64 | 9.1 |
| Example 65 | 9.0 | Example 67 | 8.7 |
| Example 68 | 8.9 | Example 69 | 10.2 |
| Example 70 | 8.8 | Example 71 | 9.6 |
| Example 72 | 10.0 | Example 73 | 9.3 |
| Example 74 | 9.3 | Example 75 | 8.7 |
| Example 76 | 9.0 | Example 77 | 9.1 |
| Example 78 | 9.0 | Example 79 | 10.2 |
| Example 80 | 9.6 | Example 81 | 10.1 |
| Example 82 | 10.0 | Example 84 | 9.5 |
| Example 87 | 8.9 | Example 88 | 9.1 |
| Example 89 | 9.9 | Example 91 | 9.0 |
| Example 93 | 10.1 | Example 94 | 9.2 |
| Example 95 | 8.8 | Example 96 | 10.0 |
| Example 97 | 10.7 | Example 99 | 9.5 |
| Example 101 | 8.9 | Example 102 | 9.3 |
| Example 103 | 8.9 | Example 104 | 9.3 |
| Example 104 | 9.5 | Example 108 | 10.1 |
| Example 109 | 10.0 | Example 111 | 9.7 |
| Example 114 | 8.8 | Example115 | 8.5 |
| Example 116 | 9.5 | Example 117 | 10.3 |
| Example 118 | 9.5 | Example 119 | 9.6 |
| Example 120 | 9.5 | Example 121 | 9.3 |
| Example 122 | 10.0 | Example 123 | 10.0 |
| Example 124 | 10.0 | Example 125 | 9.6 |

TABLE I-continued

| Compound | pKi | Compound | pKi |
|---|---|---|---|
| Example 126 | 9.8 | Example 127 | 10.1 |
| Example 128 | 9.9 | Example 129 | 10.3 |
| Example 130 | 10.3 | Example 131 | 10.4 |
| Example 132 | 10.5 | Example 133 | 10.2 |
| Example 134 | 10.2 | Example 135 | 9.8 |
| Example 136 | 10.2 | Example 137 | 10.1 |
| Example 138 | 9.8 | Example 139 | 10.1 |
| Example 141 | 9.6 | Example 145 | 9.3 |
| Example 146 | 9.4 | Example 147 | 9.2 |
| Example 148 | 9.5 | Example 149 | 9.9 |
| Example 151 | 8.9 | Example 152 | 9.9 |

The present compounds of formula (I) can be handled according to the common pharmacopoeial techniques in order to prepare formulations suitable for oral, intranasal, parentheral, sublingual, inhalatory, transdermic, local or rectal use according to the data known in literature for this kind of products; these formulations comprise oral formulations, such as tablets, capsules, powders, granulated preparations, and oral solutions or suspensions, formulations for sublingual administration, for intranasal administration, aerosol formulations, implantations, formulations for sub-cutaneous, intramuscular, intravenous, intraocular and rectal administration. The effective doses are 0.1 to 50 mg/kg of body weight. For humans the effective dose may preferably range from 0.5 to 4000 mg/day, in particular from 2.5 to 1000 mg according to the age of patients and to the type of treatment.

The treatment is performed by administering to the patient the required amount 1 to 4 times-per-day for periods of time up to 2 weeks or in any case until remission of symptoms; for chronic pathologies, administration can be prolonged for significantly longer periods of time according to the physician judgement Thanks to their high antagonist activity to tachykinins NK-2 receptor, the present compounds are useful in the treatment of diseases in which Neurokinine A plays a pathogenetic role, and namely in the following pathologies:

chronic obstructive respiratory pathologies, such as asthma and allergic rhinitis, cough, bronchitis;

ophtalmic pathologies, such as conjunctivitis or vitreoretinopathy, skin problems, such as allergic and contact dermatitis, atopic dermatitis, eczema, itch, psoriasis, burns, in particular solar burns;

intestinal disorders, such as irritable colon, ulcerous colitis, Crohn disease, diarrhoea;

gastric diseases, such as nausea or emesis;

urinary pathologies, such as prostatitis, spinal reflex bladder, urinary incontinence, cystitis, urethritis, nephritis, erectile dysfunctions;

tumoral pathologies, autoimmunitary diseases or diseases associated to AIDS;

pathologies of the nervous central system, such as anxiety, depression, schizophreny, dementia, epilepsy, Parkinson's syndrome, Alzheimer's diseases, drugs and alcohol addiction, alcoholism, Huntington's chorea, neurodegenerative diseases and somatic disorders, such as stress;

treatment of pain, in particular visceralgia, neuritis, neuralgia;

cardiovascular diseases, such as hypertension, edemas, thrombosis, angina, vascular spasmus;

inflammatory, such as arthritis, rheumatoid arthritis.

The invention claimed is:

1. Linear compounds of general formula (I)

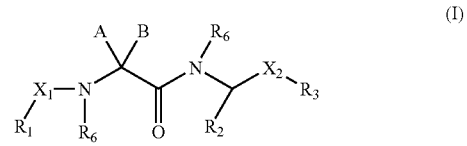

wherein:

X1 is a —CO— group;

R1 is an aromatic group selected from the group consisting of biphenyl, phenyl-ethylene, naphthyl, phenyl-thiophene, benzothiophene, benzofurane, and indole possibly N-substituted by a C1–C6 alkyl group, which can be possibly substituted by one, two or three groups independently selected from the group consisting of halogen, C1–C6 alkyl possibly substituted by not more than three fluorine atoms, C1–C6 alkyloxy, OH, NHR10, and N(R10)$_2$, wherein R10 is selected from H and C1–C6 alkyl;

R6 is H;

in the amoniacidic residue of general formula (III)

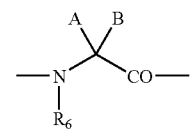

A is methyl;

B is selelected from the group consisting of ethyl and phenyl; or

A and B are joined together and form, with the carbon atom to which they are linked, a group selected from the group consisting of cyclohexyl, cyclopentyl, indanyl, cyclopent-3-enyl;

R2 is a phenyl-methyl group, having the phenyl group possibly substituted by a C1–C6 alkyl group;

X2 is selected from —CONH— and CH$_2$NH—;

R3 includes at least one basic amino group having the following formula:

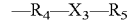

wherein:

R4 is selected from the group consisting of a group —(CH$_2$)$_n$— wherein n ranges from 1 to 3, a C5–C8 cycloalkylene group selected from cyclopentylene and cyclohexylene, and an aliphatic heterocycle selected from piperidine, pyrrolidine and piperazine possibly substituted by one or two C1–C6 alkyl groups;

X3 is a bond or it is a group selected from —CO—, —CH$_2$—, —CH$_2$—CH$_2$—, and —NH—CO—;

R5 is selected from:

a) an aliphatic heterocycle selected from the group consisting of piperidine, pyrrolidine, morpholine, diazepan, tetrahydropyran, and 1,4-dioxa-8-s7nspiro [4,5]decane, possibly substituted by one or two groups selected from C1–C6 alkyl, C1–C6 alkyloxy, OH, and cyanomethyl;

b) an azetidine substituted by a group —(CH2)$_n$—R17, wherein R17 is tetrahydropyran;

c) a piperidine possibly C-substituted by a C1–C6 alkyl group, and substituted by a group X5-R18 wherein X5 is a bond or it is selected from the group consisting of —C(R11)(R12)-, —CO—, —CH$_2$CH$_2$—, and —COCH$_2$—, and R18 is a group selected from thiophene, tetrahydropyran, tetrahydrothiopyran, pyrrolidine, cyclohexane, cyclopentane, and 1-3-dioxane, possibly substituted by one or more groups selected from C1–C6 alkyl, —NHR10, and —N(R10)$_{21}$ wherein R10, R11 and R12 are selected from H and linear or branched C1–C6 alkyl;

d) a piperazine possibly C-substituted by one or two C1–C6 alkyl group, and possibly N-substituted by a group selected from —CH$_2$CN and X4-R16, wherein X4 is a bond or it is selected from —CH$_2$— and —COCH$_2$—, and R16 is selected from the group consisting of pyridine, thiophene, tetrahydropyran, morpholine, tetrahydrofurane, and 1,3-dioxane;

e) an amino group selected from —NR11R12 and —NH—(CH$_2$)m-NR11R12, wherein R11, R12 and in are as defined above;

f) an amino-cyclohexane or a cyclohexane possibly substituted on the ring by the group —NR11R12, wherein R11 and R12 are as defined above;

g) an heteroaromatic group represented by pyridine.

2. The compounds of general formula (I) according to claim 1, wherein: X1 is a —CO— group;

R1 is an aromatic group selected from the group consisting of phenyl-ethylene, napthyl, benzothiophene, and benzofurane, possible substituted by one, two or three groups independently selected from halogen, C1–C6 alkyl possibly substituted by not more than three fluorine atoms, C1–C6 alkyloxy, OH, NHR10, and N(R10)$_2$ wherein R10 is selected from H and C1–C6 alkyl;

the amino acidic residue of general formula (III) is selected from 1-aminocyclohexane-1carboxylic acid (Ac6c), and 1-aminocyclopentane-1-carboxylic acid (Ac5c);

R6 is H;
R2 is phenyl-methyl;
X2 is —CONH—;
R3 includes at least one basic amino group and it is the following group:

—R$_4$—X$_3$—R$_5$ wherein

R4 is selected from —(CH$_2$)$_n$ wherein n ranges from 1 to 3, and piperidine possibly substituted by a C1–C6 alkyl group;

X3 is a bond or it is a group selected from —CO— and —CH$_2$—;

R5 is selected from:

a) an aliphatic heterocycle selected from piperidine and tetrahydropyran, possibly substituted by one or more C1–C6 alkyl groups;

b) a piperidine possibly C-substituted by a C1–C6 alkyl group, substituted by a group X5-R18 wherein X5 is a bond or it is a group selected from —C(R11)(R12)— and —CO—, and R18 is a group selected from tetrahydropyran, cyclohexane and 1-3-dioxane, possibly substituted by one or more groups selected from C1–C6 alkyl, -NHR10, and —N(R10)$_{21}$ wherein R10, R11 and R12 are selected from H and linear or branched C1–C6 alkyl;

c) a piperazine possibly substituted by one or two C1–C6 alkyl groups, and possibly N-substituted by a group X4-R-16 wherein X4 is —CH$_2$—, and R16 is selected from tetrahydropyran and 1,3-dioxane.

3. The compounds of general formula (I) according to claim 1, wherein the said compounds are defined by the following formulas:

N$^\alpha$[N$^\alpha$(benzo[b]thiophenyl-2-ylcarbonyl)-1-aminocyclopentane-1-carbonyl]-D-phenylalanine-N-[3(morpholin-4-yl)propyl]amide;

(1R, 3S)-acid-N$^\gamma${N$^\alpha$[N$^\alpha$(benzo[b]thiophen-2-yl-carbonyl)-1-aminocyclopentan-1-carboxy]-D-phenylalanil}-3-aminocyclopentan-1-carboxylic-N-[(1S,2S)-2-aminocyclohexyl]amide;

N$^\gamma${N$^\alpha$[N$^\alpha$(biphen-4-ylcarboxy)-1-aminocyclopentan-1-carboxy]-D-phenylalanil}-(1R,3S)-3-aminocyclopentane-1-carboxylic-acid-N-((1S,2S)-2-aminocyclohexyl)amide trifluoroacetate salt N$^\gamma${N$^\alpha$[N$^\alpha$(N-(methyl)indol-2-ylcarboxy)-1-aminocyclopentan-1-carboxy]-D-phenylalanyl}-(1R,3S)-3-aminocyclopentane-1-carboxylic-acid-N-((1S,2S)-2-amino cyclohexyl)amide trifluoroacetate salt N$^\gamma${N$^\alpha$[N$^\alpha$[4-(methyl)cynnamoyl]-1-aminocyclopentan-1-carboxy]-D-phenylalanyl}-(1R,3S)-3-aminocyclopentane-1-carboxylic-acid-N-((1S,2S)-2-aminocyclohexyl)amide trifluoroacetate salt N$^\gamma${N$^\alpha$[N$^\alpha$(benzofuran-2-ylcarboxy)-1-aminocyclopentan-1-carboxy]-D-phenylalanyl}-(1R,3S)-3-aminocyclopentane-1-carboxylic-acid-N-((1S,2S)-2-aminocyclohexyl) amide trifluoroacetate salt N$^\alpha$[N$^\alpha$(4-(methyl)cinnamoyl)-(R,S)1-aminoindane-1-carboxy]-D-phenylalanine amide-N-[(1S,3R)-3-(morpholin-4-ylmethyl)cyclopentyl]

N$^\gamma${N$^\alpha$[N$^\alpha$(benzo[b]thiophen-2-ylcarbonyl)-1-aminocyclopentan-1-carboxy]-D-phenylalanyl}-(1R, 3S)-3-aminocyclopentane-1-carboxylic-acid-N-((1S,2S)-2-dimethylaminocyclohexyl)amide hydrochloride salt N$^\gamma${N$^\alpha$[N$^\alpha$(benzo[b]thiophen-2-ylcarbonyl)-1-aminocyclopentan-1-carboxy]-D-4-methyl-phenylalanyl}-(1R, 3S)-3-aminocyclopentane-1-carboxylic-acid-N-(1S, 2S)-2-dimethylaminocyclohexyl)amide hydrochloride salt N$^\gamma${N$^\alpha$[N$^\alpha$(4-methyl-cinnamoyl)-1-aminocyclopentan-1-carboxy]-D-phenylalanyl}-(1R,3S)-3-aminocyclopentane-1-carboxylic-acid-N-((1S,2S)-2-dimethylaminocyclohexyl)amide hydrochloride salt N$^\gamma${N$^\alpha$[N$^\alpha$(benzofuran-2-ylcarboxy)-1-aminocyclopentan-1-carboxy]-D-phenylalanyl}-(1R, 3S)-3-aminocyclopentane-1-carboxylic-acid-N-((1S,2S)-2-dimethylaminocyclohexyl)amide hydrochloride salt N$^\gamma${N$^\alpha$[N$^\alpha$(biphen-4-ylcarbonyl)-1-aminocyclopentan-1-carboxy]-D-phenylalanyl}-(1R, 3S)-3-aminocyclopentane-1-carboxylic-acid-N-((1S,2S)-2-dimethylaminocyclohexyl)amide hydrochloride salt N$^\gamma${N$^\alpha$[N$^\alpha$(N-(methyl)indol-2-ylcarboxy)-1-aminocyclopentan-1-carboxy]-D-phenylalanyl}-(1R, 3S)-3-aminocyclopentane-1-carboxylic-acid-N-((1S,2S)-2-dimethylaminocyclohexyl)amide hydrochloride salt N$^\gamma${N$^\alpha$[N$^\alpha$(benzo[b]thiophen-2-ylcarbonyl)-(R)-α-methyl-α-ethylglycyl]-D-phenylalanyl}-(1R,3S)-3-aminocyclopentane-1-carboxylic-acid-N-((1S,2S)-2-aminocyclohexyl)amide trifluoroacetate salt N$^\gamma${N$^\alpha$[N$^\alpha$(4-methylcinnamoyl)-(R)-α-methyl-α-ethylglycyl]-D-phenylalanyl}-(1R,3S)-3-aminocyclopentane-1-carboxylic-acid-N-((1S,2S)-2-aminocyclohexyl)amide trifluoroacetate salt N$^\gamma${N$^\alpha$[N$^\alpha$(biphenyl-4-carboxy)-1-aminocyclopentan-1-carboxy]-R-3(4(methyl)phenyl)alanyl}-(1R,3S)-3-aminocyclopentane-1-carboxylic-acid-N-((1S,2S)-2-aminocyclohexyl)amide hydrochloride salt N^γ{N^α[N^α(N-(methyl)indol-2-ylcarboxy)-1-aminocyclopentan-1-carboxy)-R-3-(4-methyl)phenyl)alanyl}-(1R,3S)-3-aminocyclopentane-1-carboxylic-acid-N-((1S,2S)-2-aminocyclohexyl)amide hydrochloride salt N^γ{N^α[N^α(4-(methyl)cynnamoyl)-1-aminocyclopentan-1-carboxyl-R-3[4-methyl)phenyl]alanyl]-(1R,3S)-3-aminocyclopentane-1-carboxylic-acid-N-((1S,2S)-2-aminocyclohexyl)amide hydrochloride salt N^γ[N^α(benzo[b]thiophen-2-yl-carbonyl)-1-aminocyclohexan-1-carboxy]-D-phenylalanine-N-{3-[bis(n-butyl)amino]propyl}amide N^γ[N^α(benzo[b]thiophen-2-yl-carbonyl)-1-aminocyclohexan-1-carboxy]-D-phenylalanine-N-[3(morpholin-4-yl)propyl]amide acid-3-cis-N^γ{N^α[N^α(benzo[b]thiophen-2-ylcarbonyl)-1-aminocyclohexan-1-carboxy]-D-phenylalanil}aminocyclohexan-1-carboxylic-N-((1R,2S)-2-aminocyclohexyl)amide N^γ{N^α[N^α(benzo[b]thiophen-2-ylcarbonyl)-1-aminocyclohexan-1-carboxy]-D-phenylalanyl}-3-cis-aminocyclohexan-1-carboxylic-acid-N-(5-aminopentyl)-amide trifluoroacetate salt N^α[N^α(benzo[b]thiophen-2-ylcarbonyl)-1-(R)-amino-indane-1-carboxy]-D-phenylalanine-N-[3(morpholin-4-yl)propyl]amide N^α[N^α(benzo[b]thiophen-2-ylcarbonyl)-1-aminocyclopentane-1-carboxy]-L-phenylalanine-N-[3(morpholin-4-yl)propyl]amide (1R,3S)acid-3-N^γ{N^α[N^α(benzo[b]thiophen-2-ylcarbonyl)-1-aminocyclohexan-1-carboxy]-D-phenylalanil}aminocyclopentane-1-carboxylic-N-(1S,2R)-2-aminocyclohexyl) amide acid-3-cis-N^γ{N^α[N^α(benzo[b]thiophen-2-ylcarbonyl)-1-aminocyclopentano-1-carboxy]-L-phenylalanil}aminocyclohexan-1-carboxylic-N-(2-cis-aminocyclohexyl) amide N^γ{N^α[N^α(benzo[b]thiophen-2-ylcarbonyl)-1-aminocyclohexan-1-carboxy]-D-phenylalanil}-(L-(4R)amino-proline-N-(1R,2R)-aminocyclohexyl) amide acid-3-cis-N^γ{N^α[N^α(benzo[b]thiophen-2-ylcarbonyl)-1-aminocyclohexan-1-carboxy]-D-phenylalanil}-aminocyclohexan-1-carboxylic-N-[(1S,2S)-2-aminocyclohexyl]amide acid-3-cis-N^γ{N^α[N^α(benzo[b]thiophen-2-ylcarbonyl)-1-aminocyclopentan-1-carboxy]-D-phenylalanil}aminocyclohexan-1-carboxylic-N-[(1S,2R)-2-dimethylaminocyclohexyl]amide acid-3-cis-N^γ{N^α[N^α(benzo[b]thiophen-2-ylcarbonyl)-1-aminocyclopentan-1-carboxy]-D-phenylalanil}aminocyclohexan-1-carboxylic-N-[(1S,2R)-aminocyclohexyl]amide acid-3-cis-N^γ{N^α[N^α(benzo[b]thiophen-2-ylcarbonyl)-1-aminocyclopentan-1-carboxy]-D-phenylalanil}aminocyclohexan-1-carboxylic-N-[(1S,2S)-aminocyclohexyl]amide N^α[N^α(benzo[b]thiophen-2-ylcarbonyl)-1-aminocyclopentano-1-carboxy]-D-phenylalanina amide-N-[(1S,3R)-3-(4-(methyl)piperazin-1-yl)methyl)cyclopentyl]

N^α[N^α(benzo[b]thiophen-2-ylcarbonyl)-1-aminocyclopentan-1-carboxy]-D-phenylalanina amide-N-[(1S,3R)-3-(4-(methyl)piperazin-1-yl)carbonyl)cyclopentane N^α[N^α(benzo[b]thiophen-2-ylcarbonyl)-D-α-methylphenylalanil]-D-phenylalanina-N-[3-(morpholin-4-yl)propyl]amide acid-3-cis-N^α[N^α(benzo[b]thiophen-2-ylcarb(onyl)-1-aminocyclohexan-1-carboxy]-D-phenylalanil}aminocyclohexan-1-carboxylic-N-((1R,2S)-2-methylaminocyclohexyl)amide N^α[N^α(benzo[b]thiophen-2-ylcarbonyl)-1-aminocyclopentan-1-carboxy]-D-phenylalanil}-L-(4R)amino-prolina-N-(-2-cis-aminocyclohexyl)amide (1R,3S) acid-3-N^γ{N^α[N^α(benzo[b]thiophen-2-ylcarbonyl)-1-aminocyclopentan-1-carboxy]-D-phenylalanil}aminocyclopentane-1-carboxylic-N-(2-cis-aminocyclohexyl) amide (1S, 3R)-1-N{N^α[N^α(benzo[b]thiophen-2-ylcarbonyl)-1-aminocyclopentan-1-carboxyl-D-phenylalanil}-3-{[1S-((2S)-aminocyclohexyl)amino]methyl}aminocyclopentane acid-3-cis-N(N^α[N^α(benzo[b]thiophen-2-ylcarbonyl)-1-aminocyclopentan-1-carboxy]-D-phenylalanil}aminocyclohexan-1-carboxylic-N-((1R,2S)-2-dimethylaminocyclohexyl) amide (1R,3S) acid-3-N{N^α[N^α(benzo[b]thiophen-2-ylcarbonyl)-1-aminocyclohexan-1-carboxy]-D-phenylalanil}aminocyclopentan-1-carboxylic-N-((1R,2R)2-aminocyclohexyl)amide Biphenyl-4-carboxylic acid, {1-[1-(3-morpholin-4-ylpropylcarbamoyl)-2-(R)-phenyl-ethylcarbamoyl]-cyclopentyl}-amide Benzofuran-2-carboxylic acid, {1-[1-(3-morpholin-4-ylpropylcarbamoyl)-2-(R)-phenyl-ethylcarbamoyl]-cyclopentyl}-amide Benzo[b]thiophene-2-carboxylic acid, methyl-{1-[1-(3-morpholin-4-yl-propylcarbamoyl)-2(R)-phenyl-ethylcarbamoyl]-cyclohexyl}-amide 1-[3-(3,4-dichlorophenyl)-acryloylamino]-cyclopentanecarboxylic acid, [1-(3-morpholin-4-yl-propylcarbamoyl)-2-(R)-phenyl-ethyl]-amide Benzo[b]thiophene-2-carboxylic acid {1-[1R-(3-morpholin-4-yl-propylcarbamoyl)-2-phenyl-ethylcarbamoyl]-cyclopent-3-enyl}-amide 1-Methyl-1H-indole-2-carboxylic acid, {1-[1-(3-morpholin-4-yl-propylcarbamoyl)-2-(R)-phenyl-ethylcarbamoyl]-cyclopentyl}-amide Benzo[b]thiophene-2-carboxylic acid (1-{1-[3-(2,6-dimethyl-morpholin-4-yl)-propylcarbamoyl]-2-(R)-phenyl-ethylcarbamoyl}-cyclohexyl)-amide 1H-indole-2-carboxylic acid, {1-[1-(3-morpholin-4-yl-propylcarbamoyl)-2-(R)-phenylethylcarbamoyl]-cyclopentyl}-amide 1-[3-(3,4-dibromophenyl)-acryloylamino]-cyclopentanecarboxylic acid [1-(3-morpholin-4-yl-propylcarbamoyl)-2-(R)-phenyl-ethyl]-amide 5-phenyl-thiophene-2-carboxylic acid, {1-[1-(3-morpholin-4-yl-propylcarbamoyl)-2-(R)-phenyl-ethylcarbamoyl]-cyclopentyl}-amide Benzo[b]thiophene-2-carboxylic acid, (1-{1(R)-[3-(4-methyl-[1,4]diazepan-1-yl)-propylcarbamoyl]-2-phenylethyl carbamoyl}-cyclopentyl)-amide TFA salt Benzo[b]thiophene-2-carboxylic acid (1-{1(R)-[3-(4-methoxy-piperidin-1-yl)-propylcarbamoyl]-2-phenyl-ethylcarbamoyl}-cyclopentyl)-amide TFA salt Benzo[b]thiophene-2-carboxylic acid (1-{1-(R)-[3-(4-hydroxy-piperidin-1-yl)-propylcarbamoyl]-2-phenylethyl carbamoyl}-cyclopentyl)-amide, Benzo[b]thiophene-2-carboxylic acid (1-{1(R)-[3-(1,4-dioxa-8-aza-spiro[4.5]dec-8-yl)-propylcarbamoyl]-2-phenyl-ethylcarbamoyl}-cyclopentyl)-amide TFA salt Benzo[b]thiophene-2-carboxylic acid (1-{1(R)-[3-(3,5-cis-dimethylpiperazin-1-yl)-3-oxo-propylcarbamoyl]-2-phenyl-ethylcarbamoyl}-cyclopentyl)-amide TFA salt Benzo[b]thiophene-2-carboxylic acid (1-{1(R)-[3-oxo-3-(4-pyridin-2-yl-piperazin-1-yl)-propylcarbamoyl]-2-phenyl-ethylcarbamoyl}-cyclopentyl)-amide 6-Bromo-naphthalene-2ᵞcarboxylic acid (1-{1(R)-[3-oxo-3-(4-pyridin-2-yl-piperazin-1-yl)-propylcarbamoyl]-2-phenyl-ethylcarbamoyl}-cyclopentyl)-amide TFA salt 6-Bromo-benzo[b]thiophene-2-carboxylic acid (1-{1(R)-[3-oxo-3-(4-pyridin-2-yl-piperazin-1-yl)-propylcarbamoyl]-2-phenyl-ethylcarbamoyl}-cyclopentyl)-amide Benzo[b]thiophene-2-carboxylic acid [1-(1(R)-{3-oxo-3-[4-(tetrahydro-pyran-4-ylmethyl)-piperazin-1-yl]-propylcarbamoyl}-2-phenyl-ethylcarbamoyl)-cyclopentyl]-amide TFA salt Benzo[b]thiophene-2-carboxylic acid [1-(1(R)-{3-oxo-3-[4-(tetrahydro-pyran-4-yl)-piperazin-1-yl]-propylcarbamoyl}-2-phenyl-ethylcarbamoyl)-cyclopentyl]-amide TFA salt Benzo[b]thiophene-2-carboxylic acid (1-{1(R)-[3-(4-[1,3]dioxan-5-ylmethyl-piperazin-1-yl)-3-oxo-propylcarbamoyl]-2-phenyl-ethylcarbamoyl}-cyclopentyl)-amide TFA salt Benzo[b]thiophene-2-carboxylic acid [1-(1(R)-{[1-(1-amino-cyclopentanecarbonyl)-piperidin-4-ylmethyl-carbamoyl}-2-phenyl-ethylcarbamoyl)-cyclopentyl]-amide Benzo[b]thiophene-2-carboxylic acid [1-(1(R)-{[3-oxo-3-[4-(tetrahydro-furan-2(R)-ylmethyl)-piperazin-1-yl]-propylcarbamoyl}-2-phenyl-ethylcarbamoyl)-cyclopentyl]-amide TFA salt Benzo[b]thiophene-2-carboxylic acid (1-{1(R)-[3-(4-cyanomethyl-piperazin-1-yl)-3-oxo-propylcarbamoyl]-2-phenyl-ethylcarbamoyl}-cyclopentyl)-amide Benzo[b]thiophene-2-carboxylic acid {1-[2-phenyl-1(R)-(1-pyridin-2-ylmethyl-piperidin-4-ylcarbamoyl)-ethylcarbamoyl]-cyclopentyl}-amide TFA salt Benzo[b]thiophene-2-carboxylic acid [1-(2-phenyl-1(R)-{1-[2-(tetrahydro-pyran-4-yl)-ethyl]-piperidin-4-ylcarbamoyl}-ethylcarbamoyl)-cyclopentyl]-amide TFA salt 6-Bromo-naphthalene-2-carboxylic acid (1-{1R}-[(1-ethyl-piperidin-4-ylmethyl)-, carbamoyl]-2-phenyl-ethylcarbamoyl}-cyclopentyl)-amide Benzo[b]thiophene-2-carboxylic acid {1-[2-phenyl-1(R)-({1-[2-(tetrahydro-pyran-4-yl)-ethyl]-piperidin-4-ylmethyl}-carbamoyl)-ethylcarbamoyl]-cyclopentyl}-amide Benzo[b]thiophene-2-carboxylic acid (1-{1(R)-[(1-cyclohexylmethyl-piperidin-4-ylmethyl)-carbamoyl]-2-phenyl-ethylcarbamoyl}-cyclopentyl)-amide Benzo[b]thiophene-2-carboxylic acid [1-(2-phenyl-1(R)-{[1-(tetrahydro-thiopyran-4-yl)-piperidin-4-ylmethyl]-carbamoyl}-ethylcarbamoyl)-cyclopentyl]-amide TFA salt Benzo[b]thiophene-2-carboxylic acid [1-(2-phenyl-1(R)-{[1-(tetrahydro-thiopyran-4-ylmethyl)-piperidin-4-ylmethyl]-carbamoyl}-ethylcarbamoyl)-cyclopentyl]-amide 1-((E)-3-p-Tolyl-acryloylamino)-cyclopentanecarboxylic acid {2-phenyl-1(R)-[(1-thiophen-2-ylmethyl-piperidin-4-ylmethyl)-carbamoyl]-ethyl}-amide TFA salt 6-Bromo-naphthalene-2-carboxylic acid (1-{2-phenyl-1(R)-[2-(1-pyrrolidin-2(S)-ylmethyl-piperidin-4-yl)-ethylcarbamoyl]-ethylcarbamoyl}-cyclopentyl)-amide TFA salt 6-Bromo-naphthalene-2-carboxylic acid (1-{2-phenyl-1(R)-[(piperidin-4-ylmethyl)-carbamoyl]-ethylcarbamoyl}-cyclopentyl)-amide 1-(3-p-Tolyl-acryloylamino)-cyclopentanecarboxylic acid (2-phenyl-1(R)-{2-[1-(tetrahydro-pyran-4-ylmethyl)-piperidin-4-yl]-ethylcarbamoyl}-ethyl)-amide TFA salt Benzo[b]thiophene-2-carboxylic acid (1-{1(R)-[2-(1-cyanomethyl-piperidin-4-yl)-ethylcarbamoyl]-2-phenyl-ethylcarbamoyl}-cyclopentyl)-amide TFA salt Benzo[b]thiophene-2-carboxylic acid (1-{1(R)-[(1-[1,3]dioxan-5-ylmethyl-piperidin-4-ylmethyl)-carbamoyl]-2-phenyl-ethylcarbamoyl}-cyclopentyl)-amide TFA salt Benzo[b]thiophene-2-carboxylic acid (1-{1(R)-[(1-[1,3]dioxan-2-ylmethyl-piperidin-4-ylmethyl)-carbamoyl]-2-phenyl-ethylcarbamoyl}-cyclopentyl)-amide 5-Chloro-benzofuran-2-carboxylic acid [1-(2-phenyl-1(R)-{[1-(tetrahydro-pyran-4-yl)-piperidin-4-ylmethyl]-carbamoyl}-ethylcarbamoyl)-cyclopentyl]-amide 5-Chloro-benzofuran-2-carboxylic acid [1-(2-phenyl-1(R)-{[1-(tetrahydro-thiopyran-4-yl)-piperidin-4-ylmethyl]-carbamoyl}-ethylcarbamoyl)-cyclopentyl]-amide Benzo[b]thiophene-2-carboxylic acid [1-(1(R)-benzyl-2-{2-[1-(thiophen-2-yl-acetyl)-piperidin-4-yl]-ethylamino}-ethylcarbamoyl)-cyclopentyl]-amide TFA salt Benzo[b]thiophene-2-carboxylic acid [1-(1(R)-{[1-(1-amino-cyclohexanecarbonyl)-piperidin-4-ylmethyl]-carbamoyl}-2-phenyl-ethylcarbamoyl)-cyclopentyl]-amide TFA salt 6-Bromo-naphthalene-2-carboxylic acid [1-(2-phenyl-1(R)-{2-[1-(pyrrolidine-2(S)-carbonyl)-piperidin-4-yl]-ethylcarbamoyl}-ethylcarbamoyl)-cyclopentyl]-amide 6-Bromo-naphthalene-2-carboxylic acid [1-(2-phenyl-1(R)-{2-[1-(pyrrolidine-2(R)-carbonyl)-piperidin-4-yl]-ethylcarbamoyl}-ethylcarbamoyl)-cyclopentyl]-amide Benzo[b]thiophene-2-carboxylic acid [1-(2-phenyl-1(R)-{2-[4-(thiophen-2-yl-acetyl)-piperazin-1-yl]-ethylcarbamoyl}-ethylcarbamoyl)-cyclopentyl]-amide 5-Chloro-benzofuran-2-carboxylic acid {1-[1R-(3-morpholin-4-yl-propylcarbamoyl)-2-phenyl-ethylcarbamoyl]-cyclopentyl}-amide 5-Chloro-benzo[b]thiophene-2-carboxylic acid {1-[1R-(3-morpholin-4-yl-propylcarbamoyl)-2-phenyl-ethylcarbamoyl]-cyclopentyl}-amide 5-Bromo-benzofuran-2-carboxylic acid {1-[1R-(3-morpholin-4-yl-propylcarbamoyl)-2-phenyl-ethylcarbamoyl]-cyclopentyl}-amide 6-Chloro-benzo[b]thiophene-2-carboxylic acid {1-[1R-(3-morpholin-4-yl-propylcarbamoyl)-2-phenyl-ethylcarbamoyl]-cyclopentyl}-amide 6-Methoxy-benzo[b]thiophene-2-carboxylic acid {1-[1R-(3-morpholin-4-yl-propylcarbamoyl)-2-phenyl-ethylcarbamoyl]-cyclopentyl}-amide 4-Chloro-benzo[b]thiophene-2-carboxylic acid {1-[1R-(3-morpholin-4-yl-propylcarbamoyl)-2-phenyl-ethylcarbamoyl]-cyclopentyl}-amide 6-Bromo-benzo[b]thiophene-2-carboxylic acid {1-[1R-(3-morpholin-4-yl-propylcarbamoyl)-2-phenyl-ethylcarbamoyl]-cyclopentyl}-amide 6-Bromo-benzo[b]thiophene-2-carboxylic acid {1-[1R-(3-morpholin-4-yl-propylcarbamoyl)-2-phenyl-ethylcarbamoyl]-cyclohexyl}-amide 5-Fluoro-1-methyl-1H-indole-2-carboxylic acid {1-[1R-(3-morpholin-4-yl-propylcarbamoyl)-2-phenyl-ethylcarbamoyl]-cyclopentyl}-amide 6-Chloro-1-methyl-1H-indole-2-carboxylic acid {1-[1R-(3-morpholin-4-yl-propylcarbamoyl)-2-phenyl-ethyl-carbamoyl]-cyclopentyl}-amide 7-Methyl-benzo[b]thiophene-2-carboxylic acid {1-[1R-(3-morpholin-4-yl-propylcarbamoyl)-2-phenyl-ethyl-carbamoyl]-cyclopentyl}-amide 5-Methyl-benzofuran-2-carboxylic acid {1-[1R-(3-morpholin-4-yl-propylcarbamoyl)-2-phenyl-ethylcarbamoyl]-cyclopentyl}-amide 1,5-Dimethyl-1H-indole-2-carboxylic acid {1-[1R-(3-morpholin-4-yl-propylcarbamoyl)-2-phenyl-ethylcarbamoyl]-cyclopentyl}-amide 6-Amino-benzo[b]thiophene-2-carboxylic acid {1-[1R-(3-morpholin-4-yl-propylcarbamoyl)-2-phenyl-ethyl-carbamoyl]-cyclopentyl}-amide 6,7-Dichloro-benzo[b]thiophene-2-carboxylic acid {1-[1R-(3-morpholin-4-yl-propylcarbamoyl)-2-phenyl-ethylcarbamoyl]-cyclopentyl}-amide 5-tert-Butyl-benzofuran-2-carboxylic acid [1-(2-phenyl-1R-{[1-(tetrahydro-pyran-4-ylmethyl)-piperidin-4-yl-methyl]-carbamoyl}-ethylcarbamoyl)-cyclopentyl]-amide 6-Iodo-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 7-Bromo-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 7-Iodo-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 7-Methyl-benzo[b]thiophene-2-carboxylic acid [1-(2-phenyl-1R-([1-(tetrahydro-pyran-4-ylmethyl)-piperidin-4-ylmethyl]-carbamoyl}-ethylcarbamoyl)-cyclopentyl]-amide 7-Trifluoromethyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 7-Chloro-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide Benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide 1-Methyl-1H-indole-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide 7-Chloro-1-methyl-1H-indole-2-carboxylic acid [1R-(2-phenyl-1-{[1-(tetrahydropyran-4-ylmethyl)-piperidin-4-ylmethyl]-carbamoyl}-ethylcarbamoyl)-cyclopentyl]-amide 5-Chloro-3-methyl-benzofuran-2-carboxylic acid [1R-(2-phenyl-1-{[1-(tetrahydropyran-4-ylmethyl)-piperidin-4-ylmethyl]-carbamoyl}-ethylcarbamoyl)-cyclopentyl]-amide 5-Methoxy-benzofuran-2-carboxylic acid [1-(2-phenyl-1-{[1R-(tetrahydropyran-4-ylmethyl)-piperidin-4-ylmethyl]-carbamoyl}-ethylcarbamoyl)-cyclopentyl]-amide 3,5,6-Trimethyl-benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide 5-Bromo-naphthalene-2-carboxylic acid, [1-(2-phenyl-1-{[1R-(tetrahydro-pyran-4-ylmethyl)-piperidin-4-ylmethyl]-carbamoyl}-ethylcarbamoyl)-cyclopentyl]-amide Naphthalene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide Benzo[b]thiophene-2-carboxylic acid [1-(2-phenyl-1(R)-{[1-(tetrahydro-pyran-4-ylmethyl)-azetidin-3-ylmethyl]-carbamoyl}-ethylcarbamoyl)-cyclopentyl]-amide.

4. The compounds of general formula (I) according to claim 1 wherein the compounds are defined by the following formulas:

Benzo[b]thiophene-2-carboxylic acid (1-{2-phenyl-1(R)-[1-(tetrahydro-pyran-4-ylmethyl)-piperidin-4-ylcarbamoyl]-ethylcarbamoyl}-cyclopentyl)-amide TFA salt Benzo[b]thiophene-2-carboxylic acid [1-(1(R)-{2-[(1-amino-cyclohexanecarbonyl)-amino]-ethylcarbamoyl}-2-phenyl-ethylcarbamoyl)-cyclopentyl]-amide 6-Bromo-benzo[b]thiophene-2-carboxylic acid [1-(2-phenyl-1(R)-{[1-(tetrahydro-pyran-4-ylmethyl)-piperidin-4-ylmethyl]-carbamoyl}-ethylcarbamoyl)-cyclopentyl]-amide TFA salt Benzo[b]thiophene-2-carboxylic acid (1-{1-(R)-[(1-isopropyl-piperidin-4-ylmethyl)-carbamoyl]-2-phenyl-ethylcarbamoyl}-cyclopentyl)-amide Benzo[b]thiophene-2-carboxylic acid [1-(2-phenyl-1(R)-{[1-(tetrahydro-pyran-4-ylmethyl)-piperidin-4-ylmethyl]-carbamoyl}-ethylcarbamoyl)-cyclopentyl]-amide 6-Bromo-naphthalene-2-carboxylic acid [1-(2-phenyl-1(R)-{[1-(tetrahydro-pyran-4-ylmethyl)-piperidin-4-ylmethyl]-carbamoyl}-ethylcarbamoyl)-cyclopentyl]-amide Benzo[b]thiophene-2-carboxylic acid [1-(2-phenyl-1(R)-{[1-(tetrahydro-pyran-4-yl)-piperidin-4-ylmethyl]-carbamoyl}-ethylcarbamoyl)-cyclopentyl]-amide 1-(3-E-p-Tolyl-acryloyamino)-cyclopentanecarboxylic acid (2-phenyl-1(R)-{[1-(tetrahydro-pyran-4-ylmethyl)-piperidin-4-ylmethyl]-carbamoyl}-ethyl)-amide TFA salt Benzo[b]thiophene-2-carboxylic acid [1-(2-phenyl-1(R)-{2-[1-(tetrahydro-pyran-4-ylmethyl)-piperidin-4-yl]-ethylcarbamoyl}-ethylcarbamoyl)-cyclopentyl]-amide TFA salt Benzo[b]thiophene-2-carboxylic acid [1-(2-phenyl-1(R)-{2-[1-(tetrahydro-pyran-4-yl)-piperidin-4-yl]-ethylcarbamoyl}-ethylcarbamoyl)-cyclopentyl]-amide TFA salt 6-Bromo-naphthalene-2-carboxylic acid [1-(2-phenyl-1(R)-{[1-(tetrahydro-pyran-4-yl)-piperidin-4-ylmethyl]-carbamoyl}-ethylcarbamoyl)-cyclopentyl]-amide 6-Bromo-naphthalene-2-carboxylic acid (1-{1(R)-[(1-[1,3]dioxan-5-ylmethyl-piperidin-4-ylmethyl)-carbamoyl]-2-phenyl-ethylcarbamoyl}-cyclopentyl)-amide 5-Chloro-benzofuran-2-carboxylic acid (1-{1(R)-[(1-[1,3]dioxan-5-ylmethyl-piperidin-4-ylmethyl)-carbamoyl]-2-phenyl-ethylcarbamoyl}-cyclopentyl)-amide 6-Bromo-naphthalene-2-carboxylic acid [1-(1(R)-{[1-(1-amino-cyclohexanecarbonyl)-piperidin-4-ylmethyl]-carbamoyl}-2-phenyl-ethylcarbamoyl)-cyclopentyl]-amide 6-Iodo-naphthalene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Methoxy-naphthalene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Bromo-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Chloro-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 5-Fluoro-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 5-Chloro-benzofuran-2-carboxylic acid [1-(2-phenyl-1R-[1-(tetrahydro-pyran-4-ylmethyl)-piperidin-4-ylmethyl]-carbamoyl}-ethylcarbamoyl)-cyclopentyl]-amide 5-Bromo-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 7-tert-Butyl-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Methyl-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 5-Methyl-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 5-Iodo-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Chloro-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Trifluoromethyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Methoxy-benzo[b]thiophene-2-carboxylic acid [1-(2-phenyl-1R-([1-(tetrahydro-pyran-4-ylmethyl)-piperidin-4-ylmethyl]-carbamoyl}-ethylcarbamoyl)-cyclopentyl]-amide 5-Methyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Methyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide 6-Fluoro-benzo[b]thiophene-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide 6-Diethylamino-benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide 5-Diethylamino-benzofuran-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide Naphthalene-2-carboxylic acid [1-(2-phenyl-1-{[1R-(tetrahydro-pyran-4-ylmethyl)-piperidin-4-ylmethyl]-carbamoyl}-ethylcarbamoyl)-cyclopentyl]-amide 6-Bromo-naphthalene-2-carboxylic acid [1-(1(R)-{[1-(4-methyl-tetrahydro-pyran-4-ylmethyl)-piperidin-4-ylmethyl]-carbamoyl}-2-phenyl-ethylcarbamoyl)-cyclopentyl]-amide 6-Bromo-naphthalene-2-carboxylic acid [1-(1(R)-{[1-(5-ethyl-[1,3]dioxan-5-ylmethyl)-piperidin-4-ylmethyl]-carbamoyl}-2-phenyl-ethylcarbamoyl)-cyclopentyl]-amide, 6-Bromo-naphthalene-2-carboxylic acid [1-(1(R)-{[4-methyl-1-(4-methyl-tetrahydropyran-4-ylmethyl)-piperidin-4-ylmethyl]-carbamoyl}-2-phenyl-ethylcarbamoyl)-cyclopentyl]-amide, 6-Bromo-naphthalene-2-carboxylic acid [1-(1(R)-{[4-methyl-1-(tetrahydro-pyran-4-ylmethyl)-piperidin-4-ylmethyl]-carbamoyl}-2-phenyl-ethylcarbamoyl)-cyclopentyl]-amide.

5. Compounds defined by the following formulas:

benzo[b]thiophene-2-carboxylic acid, [1-(1-aminomethyl-2-(R)-phenyl-ethylcarbamoyl)-cyclohexyl]-amide benzo[b]thiophene-2-carboxylic acid {1-[2-phenyl-1(R)-(piperidin-4-ylcarbamoyl)-ethylcarbamoyl]-cyclopentyl}-amide benzo[b]thiophene-2-carboxylic acid (1-{2-phenyl-1(R)-[(piperidin-4-yl-methyl)-carbamoyl]-ethylcarbamoyl}-cyclopentyl)-amide benzo[b]thiophene-2-carboxylic acid {1-[2-phenyl-1(R)-(2-piperidin-4-yl-ethylcarbamoyl)-ethylcarbamoyl]-cyclopentyl}-amide TFA salt benzo[b]thiophene-2-carboxylic acid [1-(2-phenyl-1(R)-{2-[4-(tetrahydro-pyran-4-ylmethyl)-piperazin-1-yl]-ethylcarbamoyl}-ethylcarbamoyl)-cyclopentyl]-amide TFA salt.

6. A method of treating respiratory pathologies with the compounds of general formula (I) according to claim 5, comprising the steps of preparing pharmaceutical formulations with compounds of general formula (I) and administration of the formulations via oral, intranasal, parentheral, sublingual, inhalatory, transdermic, local and/or rectal, the respiratory pathologies selected from asthma and allergic rhinitis selected.

7. Pharmaceutical formulations comprising as the active principle at least one compound of general formula (I) according to claim 1, or mixtures thereof.

8. The pharmaceutical formulations according to claim 7, further comprising pharmaceutically acceptable diluents and excipients.

9. The pharmaceutical formulations according to claim 8, for the treatment of respiratory pathologies selected from asthma and allergic rhinitis, intestinal disorders selected from irritable colon, ulcerous colitis and Chron disease, and urinary diseases selected from cystitis and incontinence.

10. A method of treating intestinal disorders with the compounds of general formula (I) according to claim 5, comprising the steps of preparing pharmaceutical formulations with compounds of general formula (I) and administration of the formulations via oral, intranasal, parentheral, sublingual, inhalatory, transdermic, local and/or rectal, the intestinal disorders selected from irritable colon, ulcerous colitis and Chron disease.

11. A method of treating urinary diseases with the compounds of general formula (I) according to claim 5, comprising the steps of preparing pharmaceutical formulations with compounds of general formula (I) and administration of the formulations via oral, intranasal, parentheral, sublingual, inhalatory, transdermic, local and/or rectal, the urinary diseases selected from cystitis and incontinence.

* * * * *